United States Patent
Zergiebel et al.

(10) Patent No.: US 10,893,886 B2
(45) Date of Patent: Jan. 19, 2021

(54) MULTI-PORT ACCESS DEVICE FOR MINIMALLY INVASIVE SURGICAL PROCEDURES

(71) Applicant: Surgiquest, Inc., Milford, CT (US)

(72) Inventors: Earl M. Zergiebel, Guilford, CT (US); Ralph Stearns, Bozrah, CT (US)

(73) Assignee: Conmed Corporation, Utica, NY (US)

( * ) Notice: Subject to any disclaimer, the term of this patent is extended or adjusted under 35 U.S.C. 154(b) by 74 days.

(21) Appl. No.: 16/102,933

(22) Filed: Aug. 14, 2018

(65) Prior Publication Data

US 2018/0353205 A1 Dec. 13, 2018

Related U.S. Application Data

(62) Division of application No. 15/253,255, filed on Aug. 31, 2016, now Pat. No. 10,076,358.

(60) Provisional application No. 62/212,776, filed on Sep. 1, 2015.

(51) Int. Cl.
| | |
|---|---|
| *A61B 17/02* | (2006.01) |
| *A61B 17/34* | (2006.01) |
| *A61M 13/00* | (2006.01) |
| *A61B 17/00* | (2006.01) |

(52) U.S. Cl.
CPC ...... *A61B 17/3423* (2013.01); *A61B 17/0218* (2013.01); *A61B 17/0293* (2013.01); *A61B 17/3462* (2013.01); *A61B 17/3474* (2013.01); *A61M 13/003* (2013.01); *A61B 2017/00991* (2013.01); *A61B 2017/3437* (2013.01); *A61B 2017/3443* (2013.01); *A61B 2017/3445* (2013.01); *A61B 2017/3466* (2013.01); *A61M 2205/3331* (2013.01)

(58) Field of Classification Search
CPC ............ A61B 17/3423; A61B 17/3425; A61B 17/3427; A61B 17/3429
See application file for complete search history.

(56) References Cited

U.S. PATENT DOCUMENTS

| | | | |
|---|---|---|---|
| 3,612,323 A | | 10/1971 | Malick |
| 4,752,013 A | | 6/1988 | Miller et al. |
| 5,545,179 A | * | 8/1996 | Williamson, IV ............ A61B 17/3423 600/32 |
| 5,918,752 A | | 7/1999 | Meyer |
| 8,657,740 B2 | | 2/2014 | Bonadio et al. |
| 9,028,402 B2 | | 5/2015 | Wenchell |
| 9,095,300 B2 | | 8/2015 | Bonadio et al. |
| 2002/0156432 A1 | | 10/2002 | Racenet et al. |
| 2005/0222582 A1 | | 10/2005 | Wenchell |

(Continued)

FOREIGN PATENT DOCUMENTS

EP 2226027 A1 9/2010

OTHER PUBLICATIONS

Partial International Search Report dated Nov. 17, 2016 in connection with PCT/US2016/049613.

*Primary Examiner* — Jan Christopher L Merene
(74) *Attorney, Agent, or Firm* — Locke Lord LLP; Scott D. Wofsy

(57) ABSTRACT

An access device for surgical procedures is disclosed which includes a multiport end cap including a plurality of separate access ports for accommodating the introduction of individual surgical instruments into a body cavity or lumen of a patient, and a coupling for operatively connecting the multiport end cap to a tubular body.

10 Claims, 32 Drawing Sheets

(56) References Cited

U.S. PATENT DOCUMENTS

| | | | |
|---|---|---|---|
| 2008/0011307 A1* | 1/2008 | Beckman | A61B 17/02 |
| | | | 128/850 |
| 2008/0208222 A1 | 8/2008 | Beckman et al. | |
| 2008/0221607 A1 | 9/2008 | White et al. | |
| 2010/0081882 A1 | 4/2010 | Hess et al. | |
| 2010/0185057 A1 | 7/2010 | Stearns et al. | |
| 2010/0204548 A1* | 8/2010 | Bonadio | A61B 17/0218 |
| | | | 600/201 |
| 2010/0228091 A1* | 9/2010 | Widenhouse | A61B 17/0218 |
| | | | 600/203 |
| 2010/0228092 A1 | 9/2010 | Ortiz et al. | |
| 2011/0028794 A1* | 2/2011 | Widenhouse | A61B 17/0293 |
| | | | 600/208 |

\* cited by examiner

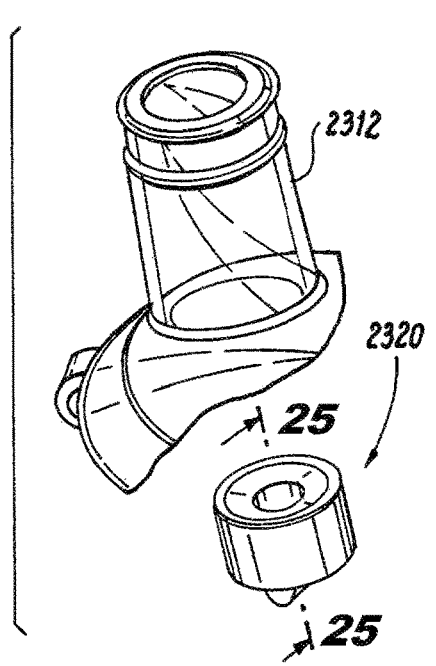
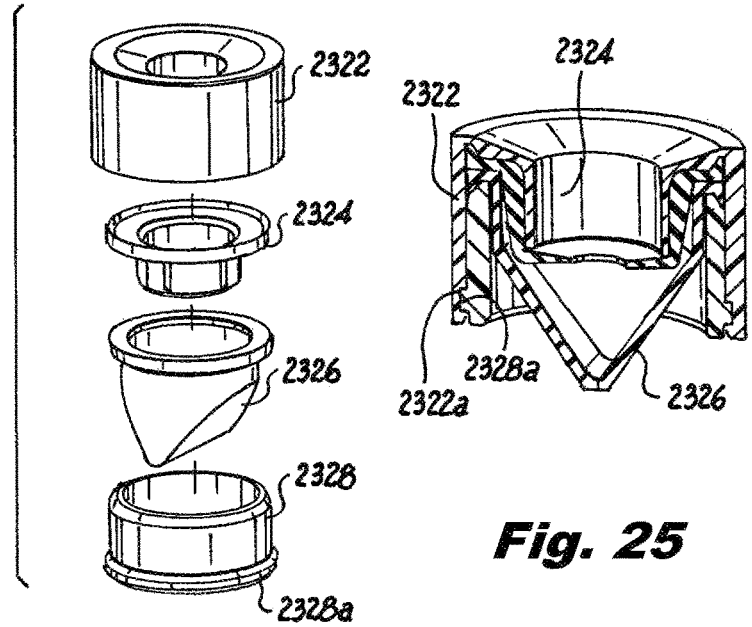
Fig. 23  Fig. 24  Fig. 25
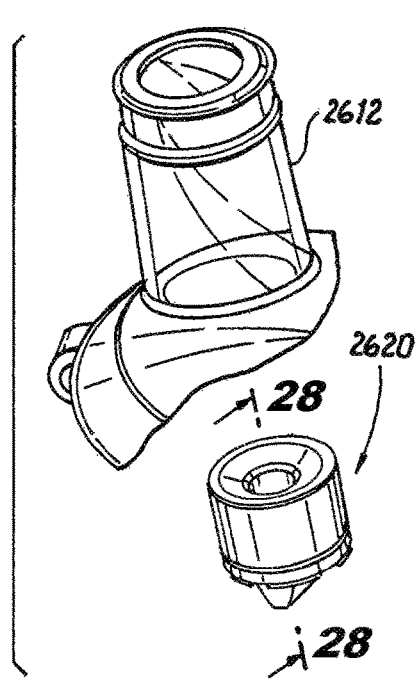
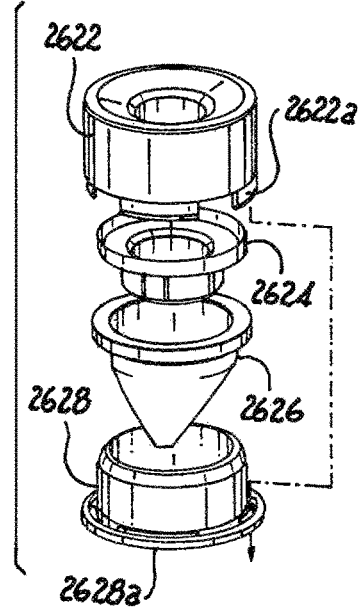
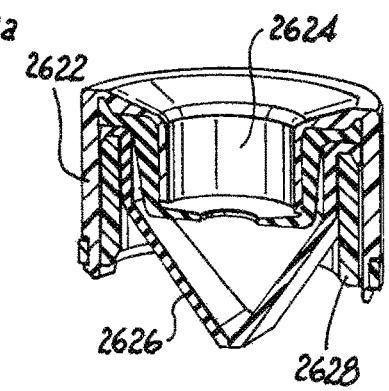
Fig. 26  Fig. 27  Fig. 28

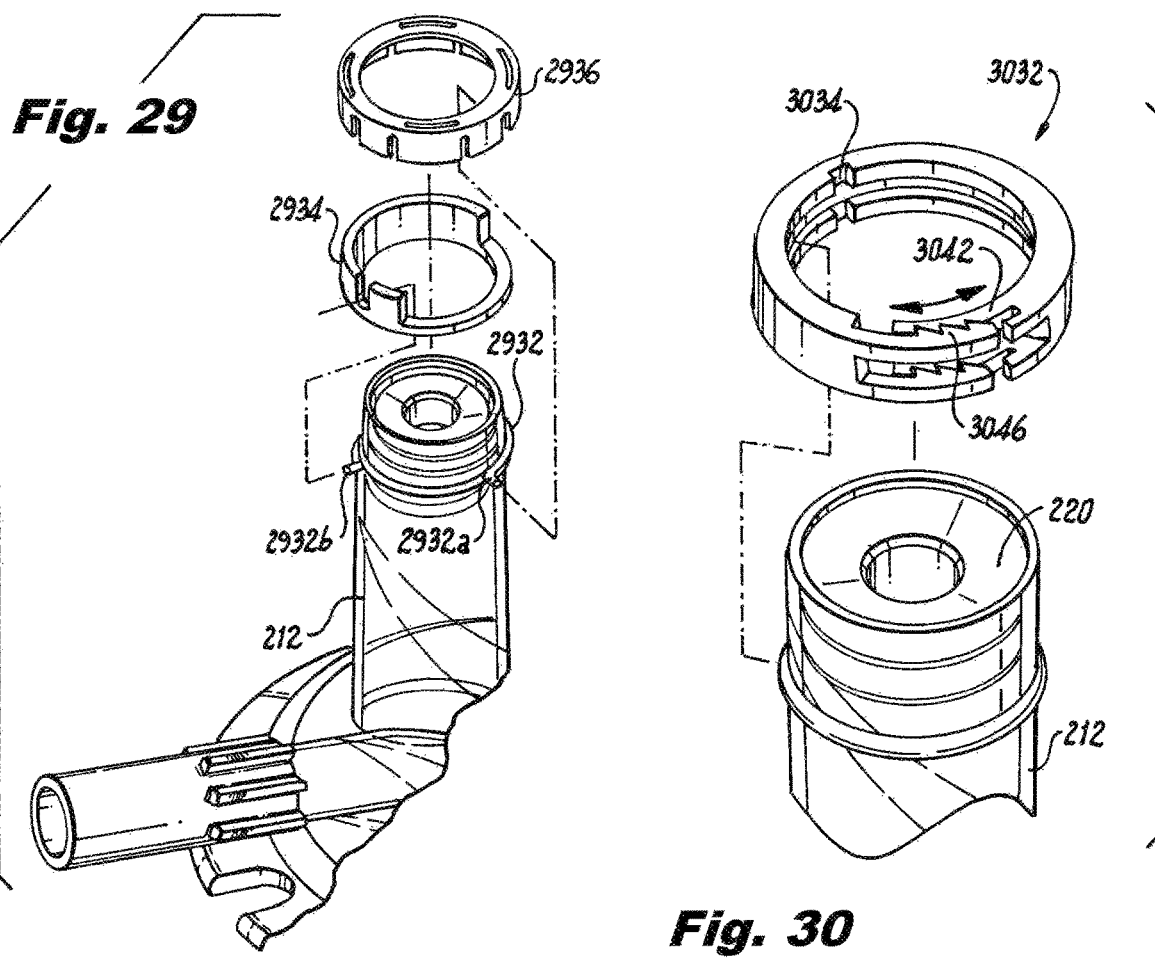
Fig. 29
Fig. 30
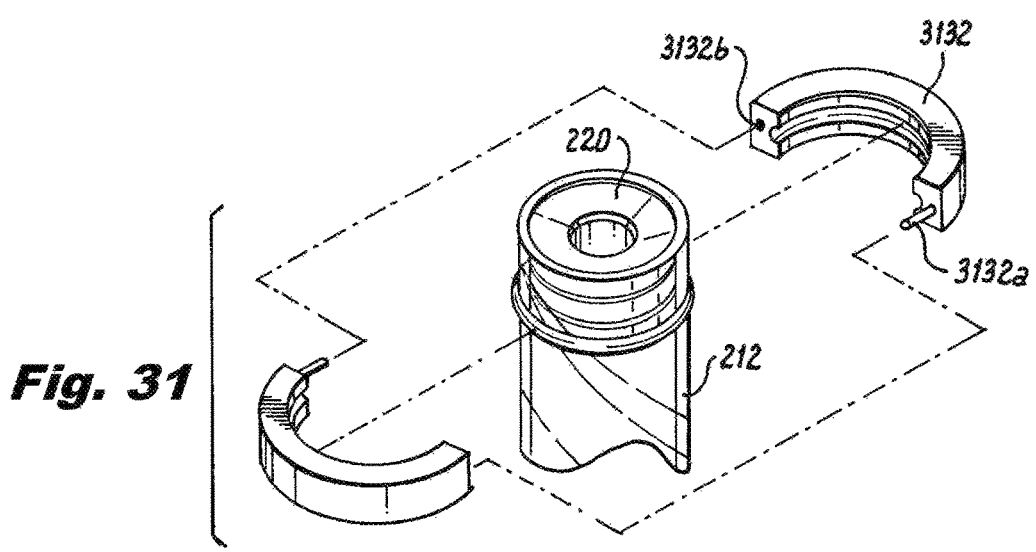
Fig. 31

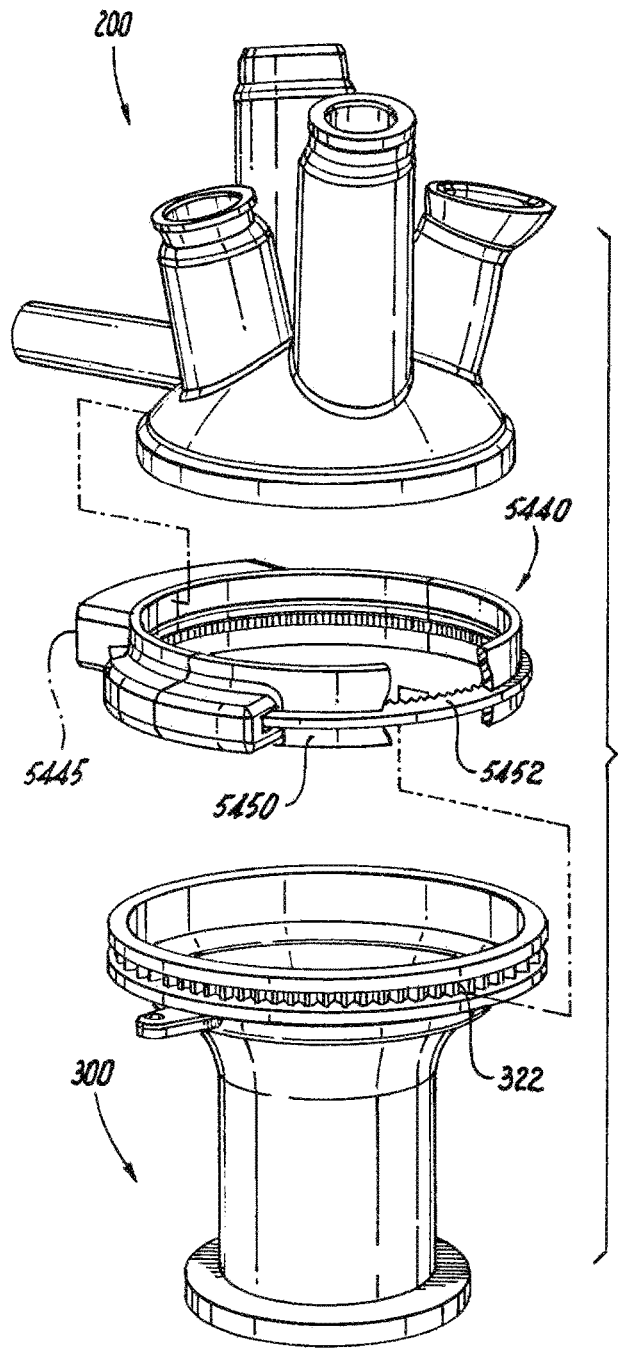
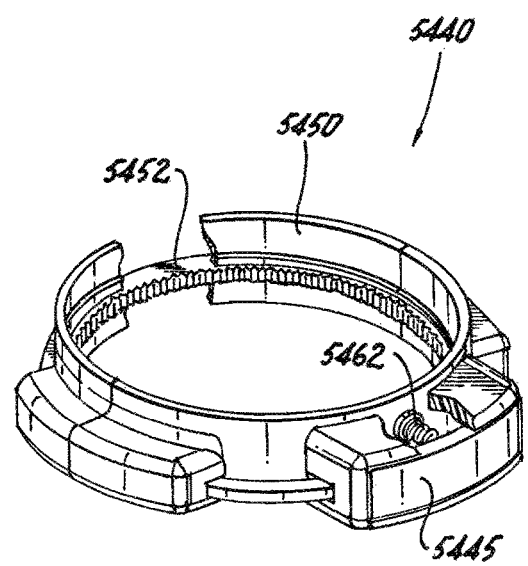
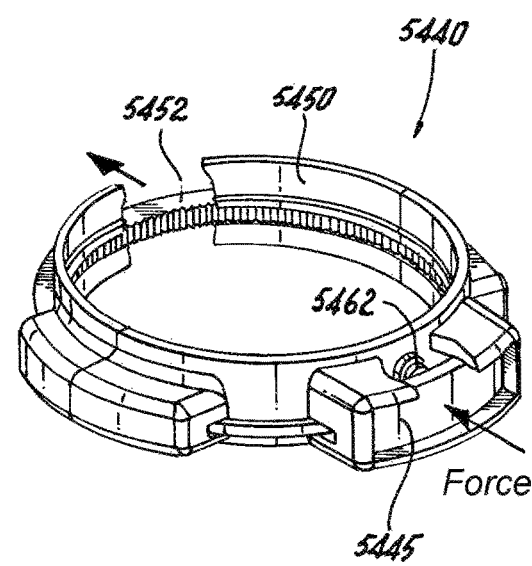
Fig. 54
Fig. 55
Fig. 56

Fig. 58
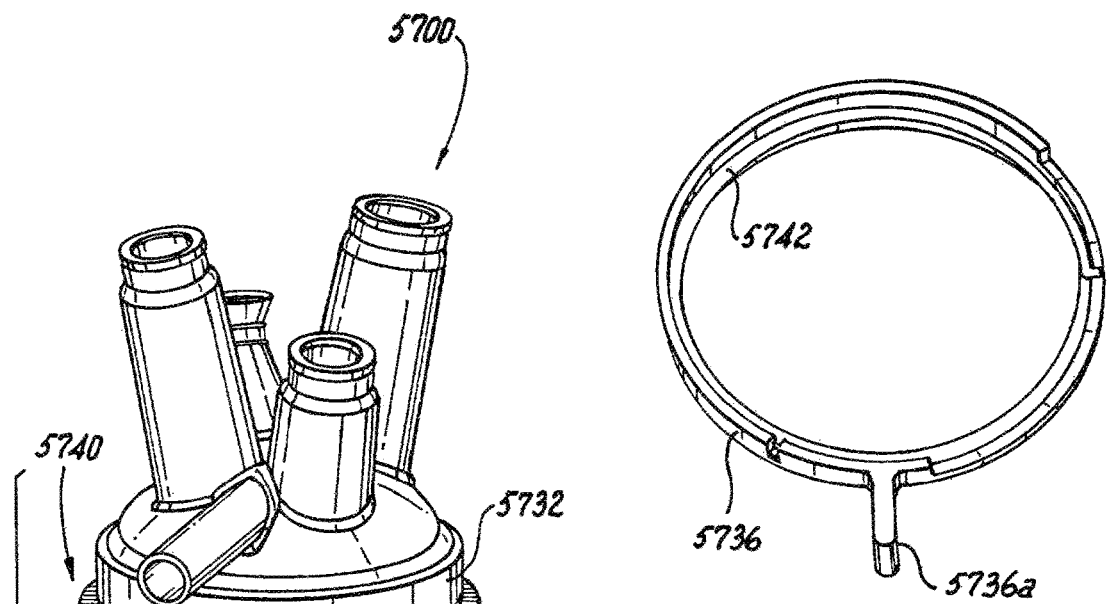
Fig. 57
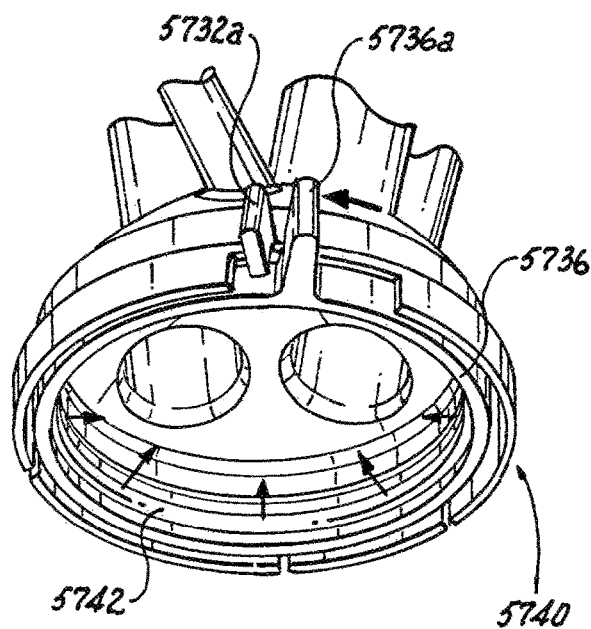
Fig. 59

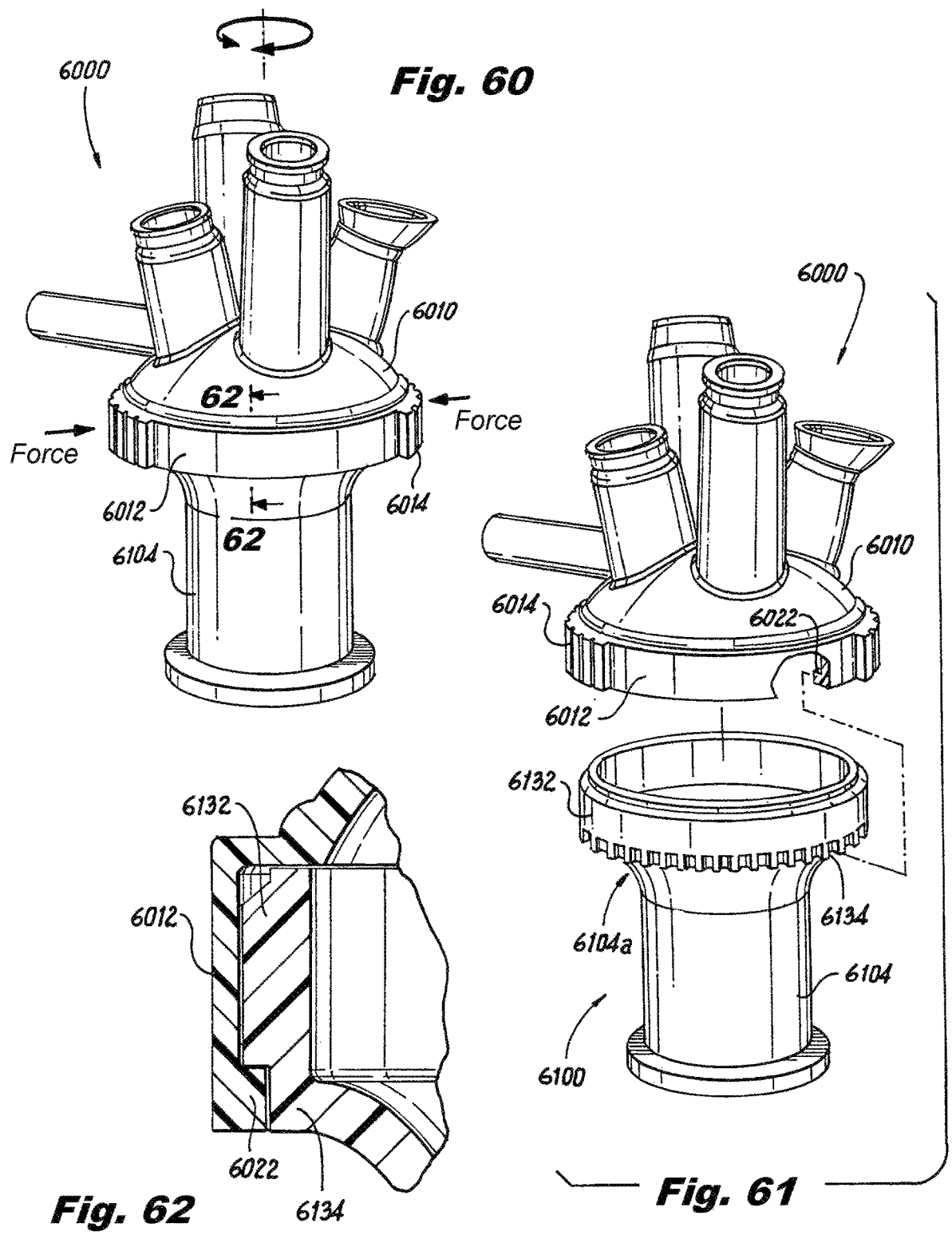

Force

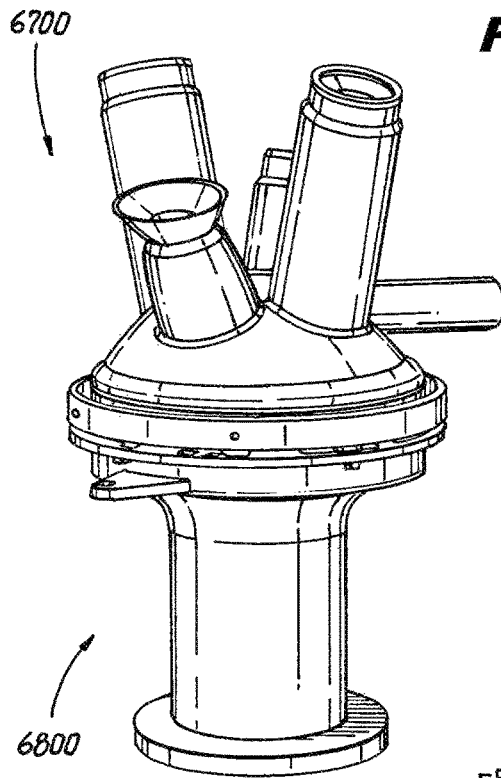
Fig. 67
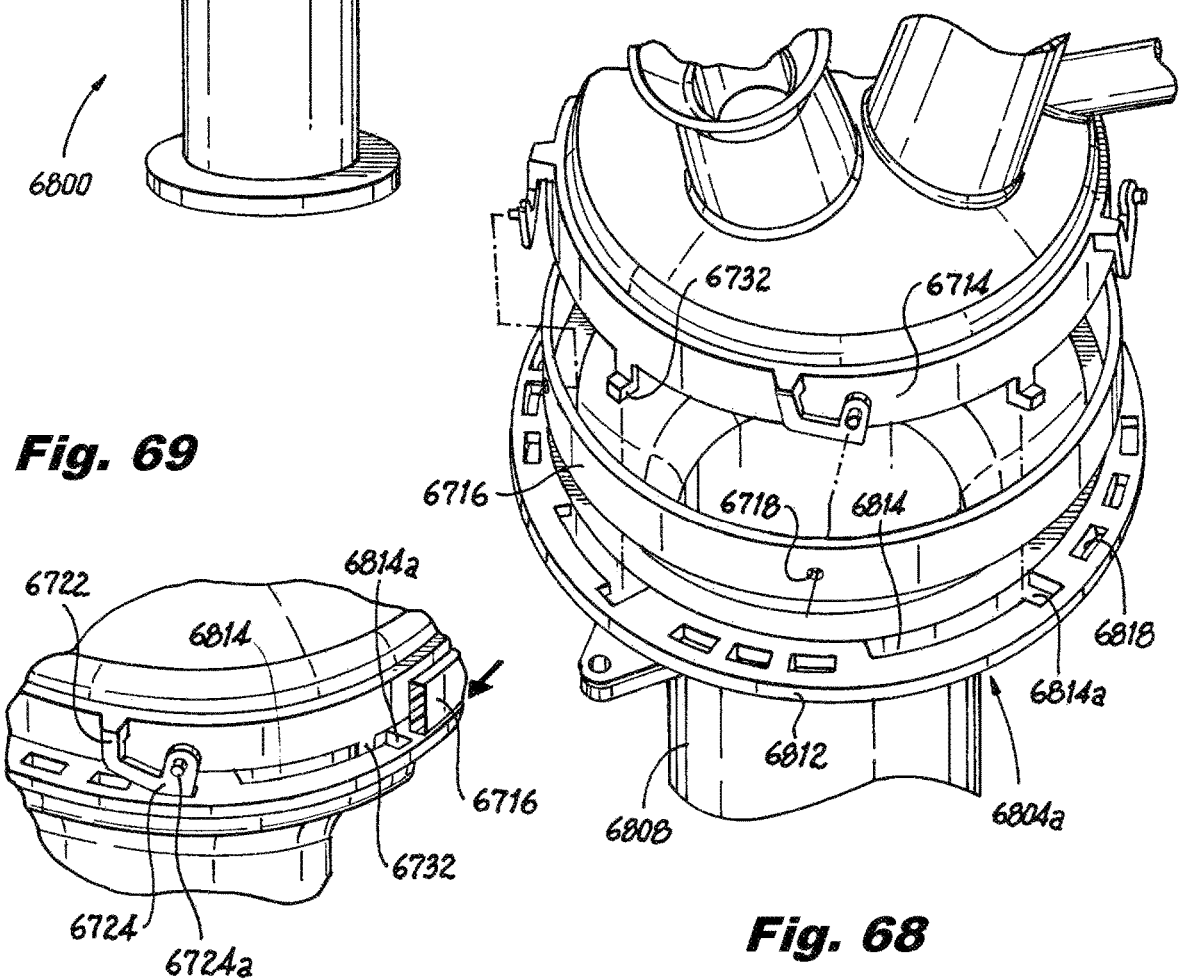
Fig. 69
Fig. 68

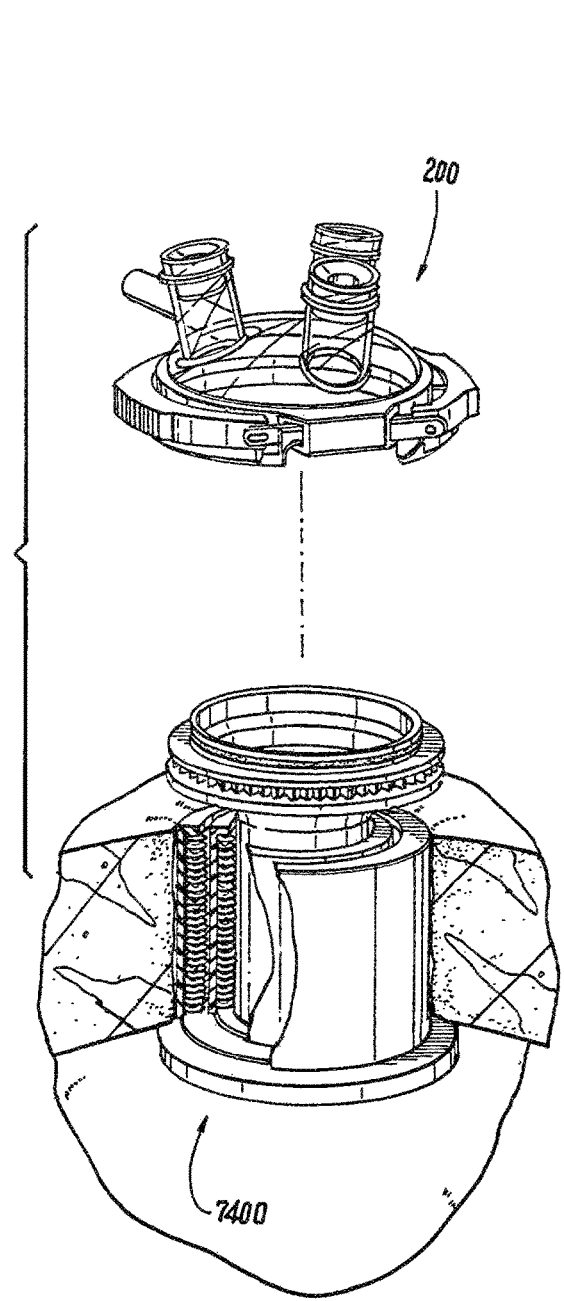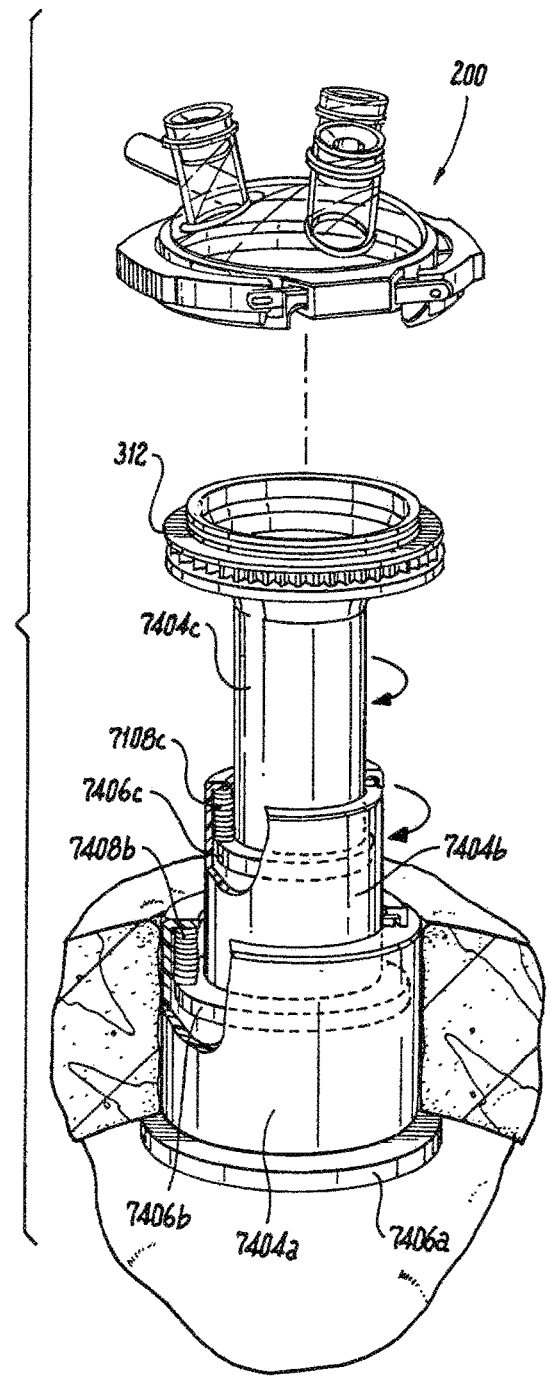
Fig. 74
Fig. 75

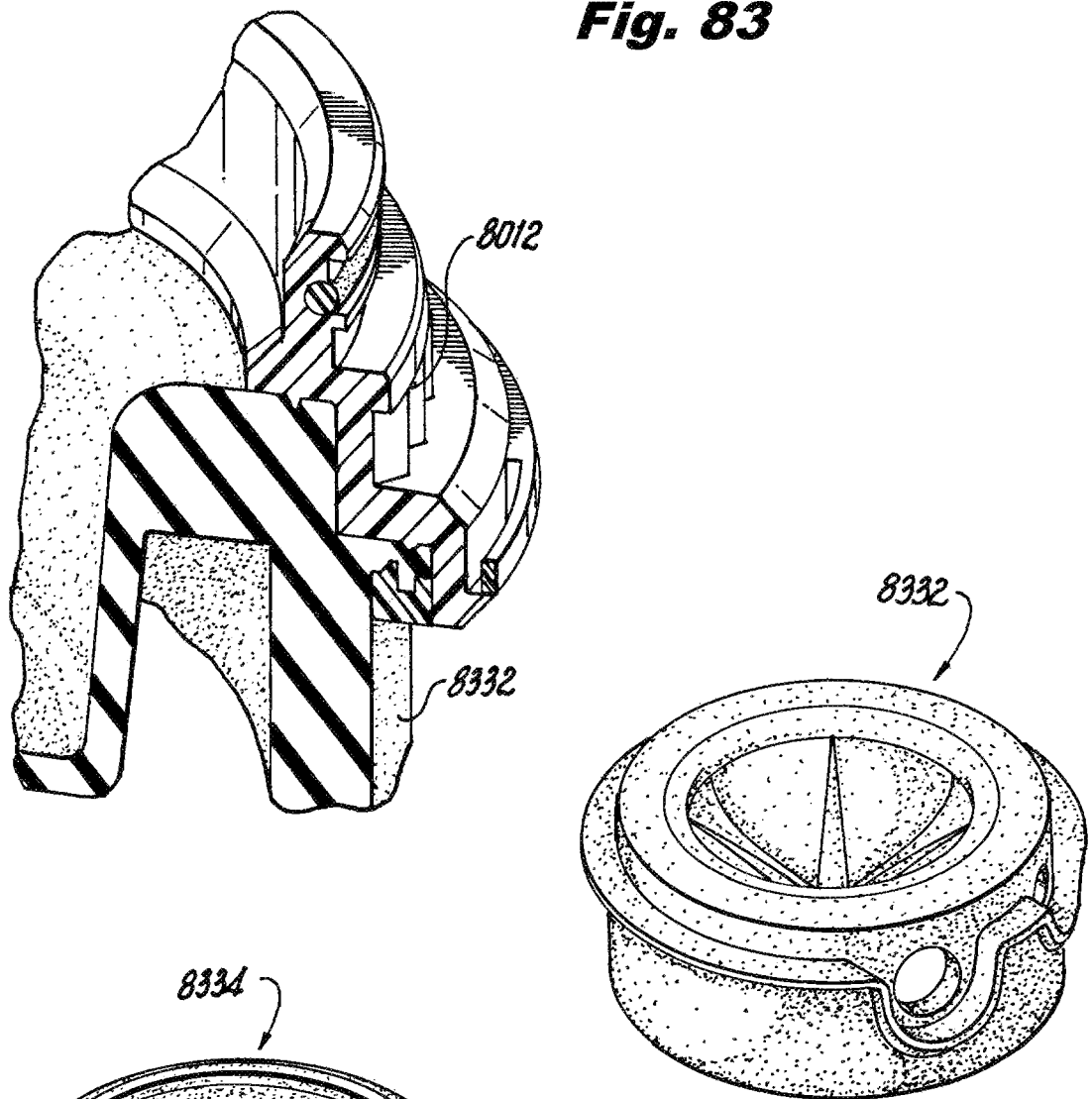
Fig. 83
Fig. 84
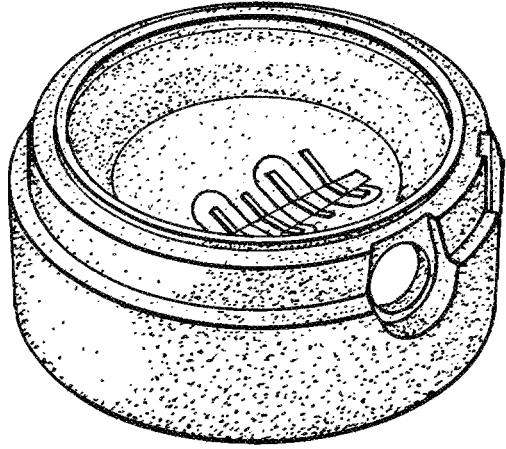
Fig. 85

MULTI-PORT ACCESS DEVICE FOR MINIMALLY INVASIVE SURGICAL PROCEDURES

CROSS-REFERENCE TO RELATED APPLICATIONS

This Application is a Continuation of U.S. patent application Ser. No. 15/253,255, filed on Aug. 31, 2016, now U.S. Pat. No. 10,076,358, issued Sep. 18, 2018, which claims the benefit of priority from U.S. Provisional Patent Application No. 62/212,776 filed on Sep. 1, 2015, the contents of which are incorporated herein by reference in their entirety.

BACKGROUND OF THE INVENTION

1. Field of the Invention

The subject invention is directed to surgical access devices, and more particularly, to a multi-port access device for minimally invasive surgical procedures including single incision laparoscopic procedures.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures commonly involve filling or "insufflating" the abdominal (peritoneal) cavity with a pressurized fluid, such as carbon dioxide, to create what is referred to as a pneumoperitoneum.

The insufflation can be carried out by a surgical access device equipped to deliver insufflation fluid, or by a separate insufflation device, such as an insufflation (veress) needle. SurgiQuest, Inc., Milford, Conn. has developed unique surgical access devices that permit ready access to an insufflated surgical cavity without the need for conventional mechanical seals, and it has developed related gas delivery systems for providing sufficient pressure and flow rates to such access devices, as described in whole or in part in U.S. Pat. Nos. 7,854,724 and 8,795,223, the disclosures of which are both herein incorporated by reference in their entireties.

During typical laparoscopic procedures, a surgeon makes three to four small incisions, usually no larger than about twelve millimeters each, which are made with the surgical access devices themselves, typically using a separate inserter or obturator placed therein. Following insertion, the inserter is removed, and the trocar allows access for instruments to be inserted into the abdominal cavity.

A variety of larger access devices are also known in the art for accessing a surgical site through a single relatively large incision to perform minimally invasive procedures, rather than through multiple small incisions. Examples of such devices are disclosed in U.S. Patent Application Publication No. 2013/0012782, the disclosure of which is herein incorporated by reference in its entirety.

It would be beneficial to provide a single incision access device having multiple ports with a variety of different port sizes to give a surgeon more options for instrument introduction during a laparoscopic surgical procedure. It would also be beneficial to provide an access device having multiple ports with a variety of different port size that enables ready access to natural orifices for performing trans-anal minimally invasive surgical procedures or the like.

SUMMARY OF THE INVENTION

The subject invention is directed to a new and useful access device for surgical procedures. The device includes an elongated tubular body portion defining a longitudinal axis which is configured for introduction through a natural orifice of a body lumen or through a single incision formed in the wall of the abdominal cavity of a patient. The device further includes a multiport end cap operatively associated with a proximal end portion of the tubular body portion and including a plurality of separate access ports for accommodating the introduction of individual surgical instruments into the body lumen or abdominal cavity of the patient. A coupling is provided for operatively connecting the multiport end cap to the proximal end portion of the tubular body portion.

Preferably, the coupling is adapted and configured to permit relative axial rotation of the multiport end cap and tubular body portion. The coupling includes a ratchet mechanism for selectively positioning the multiport end cap relative to the tubular body portion. The coupling also includes spring loaded latches for selectively moving the ratchet mechanism. In one embodiment of the invention, the coupling also includes a connector for a pressurized gas line and a connector for a pressure sensing line having a lumen extending from the pressure sensing line through a bottom surface thereof. In another embodiment, the end cap includes a connector for a pressurized gas line and the tubular body portion includes a connector for a pressure sensing line.

Preferably, a seal assembly is operatively associated with each of the access ports of the end cap, and each seal assembly includes a main orifice seal and a secondary duckbill seal, and at least one of the access ports has a larger access diameter than the other access ports. The seal assembly can be secured within each access port with an external retaining feature. The retaining feature can include a locking mechanism selected from the group consisting of hooks, ratchet teeth, pins and holes, pins and slots, I-beams and pull and twist ties. In one embodiment, the end cap can also include a trocar port.

The multiport end cap can further include a weave layer to secure surgical instruments therethrough. In one embodiment, an assembly aid can assist is engaging multiport cap with the tubular body portion. In another embodiment, the tubular body portion can have an adjustable length.

The subject invention is also directed to an access device for surgical procedures that includes a tubular adapter having opposed proximal and distal end portions, a multiport end cap including a plurality of separate access ports for accommodating the introduction of individual surgical instruments into the body lumen or abdominal cavity of the patient, a coupling for operatively connecting the multiport end cap to the proximal end portion of the tubular body portion, and a laparoscopic wound protector operatively associated with the distal end portion of the tubular adapter for introduction through a single incision formed in the wall of the abdominal cavity of a patient. In one embodiment of the device, a duckbill seal is operatively associated with the tubular adaptor. In another embodiment of the device, a generally S-shaped seal is operatively associated with the tubular adaptor.

The subject invention is also directed to an access device for surgical procedures that includes a top ring having a plurality of circumferentially spaced apart openings extending therethrough. A latch assembly including diametrically opposed latches having a plurality of circumferentially spaced apart flexible tabs is configured to snap fit into corresponding openings of the top ring. A multiport end cap is operatively secured between the top ring and the latch assembly and includes a plurality of separate access ports for accommodating the introduction of individual surgical instruments into the body lumen or abdominal cavity of the patient. A retaining ring is operatively associated with the latch assembly and is configured to permit relative axial rotation of the multiport end cap. The retaining ring has a plurality of circumferentially spaced apart flexible tabs. A bottom ring has a plurality of circumferentially spaced apart openings extending therethrough for accepting corresponding flexible tabs of the retaining ring therein. An adapter is operatively secured between the retaining ring and the bottom ring. In one embodiment, the adapter is a duck bill seal. In another embodiment, the adapter is a seal having a generally S shape.

Preferably, an elongated tubular body portion can extend distally from the adapter configured for introduction through a natural orifice of a body lumen or through a single incision formed in the wall of the abdominal cavity of a patient.

Preferably, the retaining ring includes a first connector for a pressurized gas line and a connector for a second pressure sensing line. The retaining ring can further include an O-ring seal positioned within an annular groove thereof. The retaining ring can also include a ratchet mechanism for selectively positioning the multiport end cap relative to the adapter. In one embodiment, a plurality of suture tie down flanges extends outwardly from the bottom ring.

These and other features of the subject invention and the manner in which it is manufactured and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject invention appertains will readily understand how to make and use the access devices of the subject invention without undue experimentation, preferred embodiments thereof will be described in detail herein below with reference to certain figures, wherein:

FIG. 23 is a perspective view of an alternate embodiment of a port for the multi-port sub assembly;

FIG. 24 is an exploded view of the port of FIG. 23, showing main seal and duck bill seal between a top and bottom;

FIG. 25 is a cross-sectional view taken along line 25-25 of FIG. 23, showing an assembled port of the embodiment of FIG. 23;

FIG. 26 is a perspective view of an alternate embodiment of a port for the multi-port access device;

FIG. 27 is an exploded view of the port of FIG. 26, showing flexible tabs and slots;

FIG. 28 is a cross-sectional view taken along line 28-28 of FIG. 26, showing an assembled port of the embodiment of FIG. 26;

FIG. 29 is an exploded view of an alternate embodiment for a retaining feature of the access port, showing a spring hose clamp;

FIG. 30 is an exploded view of an alternate embodiment for a retaining feature of the access port, showing a living hinge and ratchet teeth closure;

FIG. 31 is an exploded view of an alternate embodiment for a retaining feature of the access port, showing a belt closure with a pin and hole;

FIG. 54 is an exploded view of an alternate embodiment of a latch assembly for a multi-port access device, showing a spring loaded ratchet ring;

FIG. 55 is a perspective view of the ratchet ring of FIG. 55 in an uncompressed position;

FIG. 56 is a perspective view of the ratchet ring of FIG. 55 in a compressed position;

FIG. 57 is an exploded perspective view of an alternate embodiment of a latch assembly for a multi-port access device, showing a spring loaded hose clamp;

FIG. 58 is a perspective view of the hose clamp of FIG. 58, showing alignment of an inner ring and an outer ring;

FIG. 59 is a perspective view of the hose clamp of FIG. 58, showing compression of the outer ring;

FIG. 60 is a perspective view of an alternate embodiment of a latch assembly for a multi-port access device, showing a top ring having release pads;

FIG. 61 is an exploded view of the embodiment of FIG. 60, showing a ratchet feature of the top ring;

FIG. 62 is a cross sectional view taken along line 62-62 of FIG. 60, showing the ratchet feature aligned with slots of wound protector;

FIG. 67 is a perspective view of an alternate embodiment of a latch assembly for a multi-port access device, showing an outer release ring and a bottom ring;

FIG. 68 is an exploded perspective view of the multi-port access device of FIG. 67, showing flexible arms of an inner ring;

FIG. 69 is a perspective view of the multi-port access device of FIG. 67, showing locking tabs inserted into a slot of bottom ring;

FIG. 74 is an exploded perspective view of an alternate embodiment of a multi-port access device, showing a telescoping wound protector;

FIG. 75 is a perspective view of the multi-port access device of FIG. 74, showing the wound protector fully extended;

FIG. 83 is a detailed view of alignment of the multi-port sub assembly and wound protector assembly with air seal port;

FIG. 84 is a perspective view of a duck bill seal for use in the multi-port access device of FIG. 81; and FIG. 85 is a perspective view of a generally S shaped seal for use in the multi-port access device of FIG. 81.

DETAILED DESCRIPTION OF PREFERRED EMBODIMENTS

Figure 1:
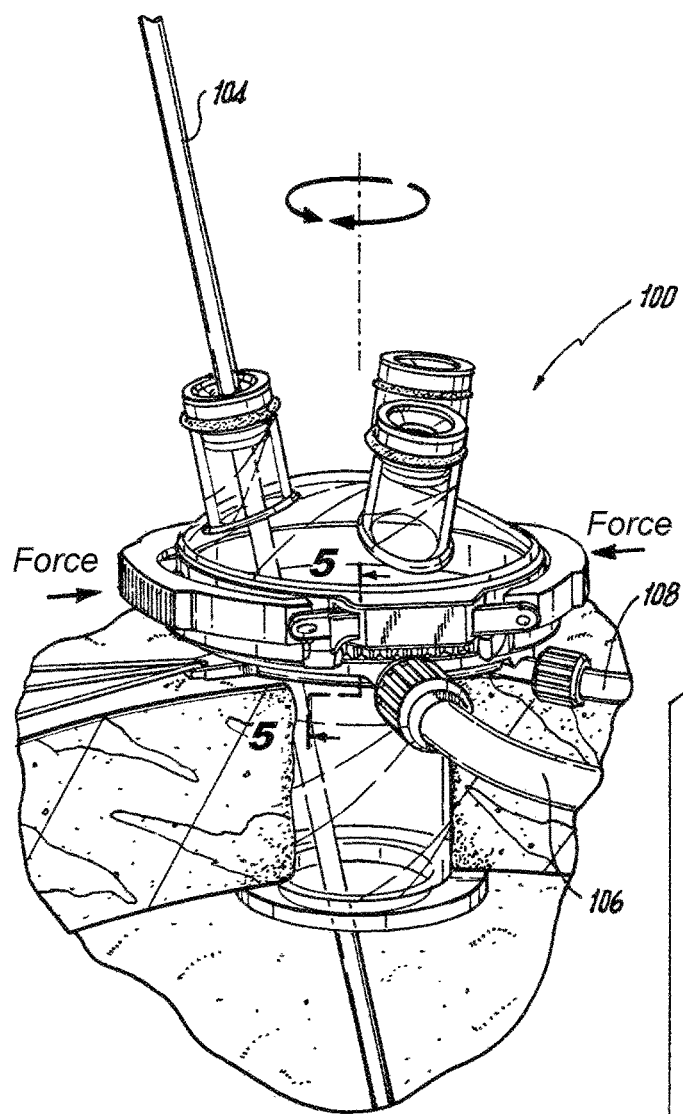
FIG. 1 is a perspective view of a multi-port access device for use in trans-anal surgical procedures in accordance with the subject invention, showing a fully assembled access device connected to an air seal line and a sense tube with a surgical device extending therethrough.

Referring now to the drawings wherein like reference numerals identify similar structural features and/or elements of the subject matter disclosed herein, there is illustrated in FIG. 1 a multi-port access device for single incisions minimally invasive surgical procedures in accordance with a preferred embodiment of the subject invention and designated generally by reference numeral 100. It will be understood by those skilled in the art that embodiments of the multi-port access device shown and described herein can be used for any procedure through a single opening or incision including, but not limited to, rectal (TAMIS) procedures and laparoscopic procedures.

With reference to FIG. 1, a fully assembled multi-port access device 100 is shown positioned within a single opening of a patient. The access device 100 allows for a plurality of surgical instruments 104 to be inserted through one incision or natural body lumen providing more options for a surgeon. Also, using natural orifices when possible improves the patient's recovery time, pain and discomfort. The access device 100 is configured and designed to cooperate with an air seal line 106 and a sensing line 108 during a surgical procedure.

Figure 2:
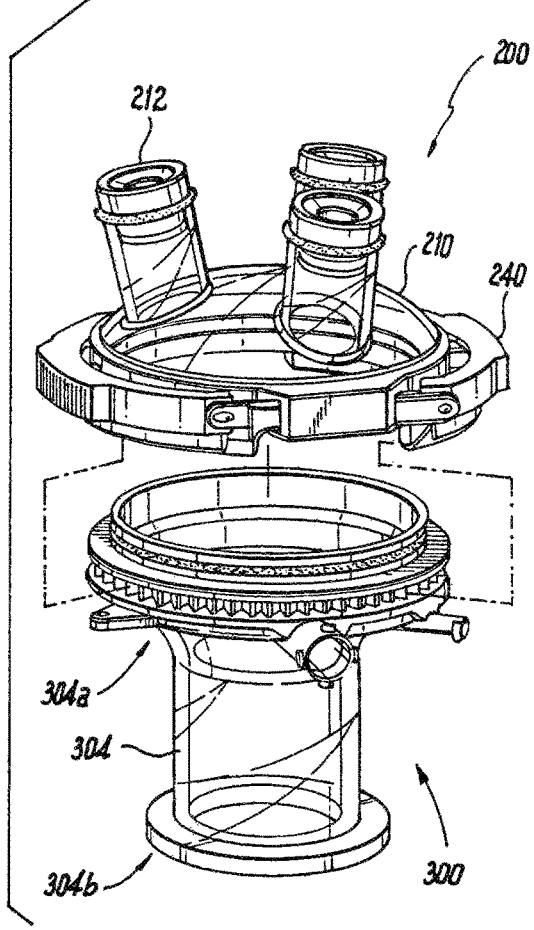
FIG. 2 is an exploded view of the multi-port access device, showing a multi-port sub assembly and a wound protector sub assembly.

As best shown in FIG. 2, the access device 100 includes a multi-port assembly 200 coupled to a wound protector assembly 300. The wound protector assembly 300 is generally an elongated tubular body portion 304 defining a longitudinal axis. The multi-port assembly 200 is operatively associated with a proximal end portion 304a of the tubular body portion 300. A coupling connects the multi-port assembly 200 and wound protector assembly 300 and is configured to allow 360 degree rotation of the multi-port assembly 200 without moving the air seal 106 or pressure sensing lines 108.

Figure 3:
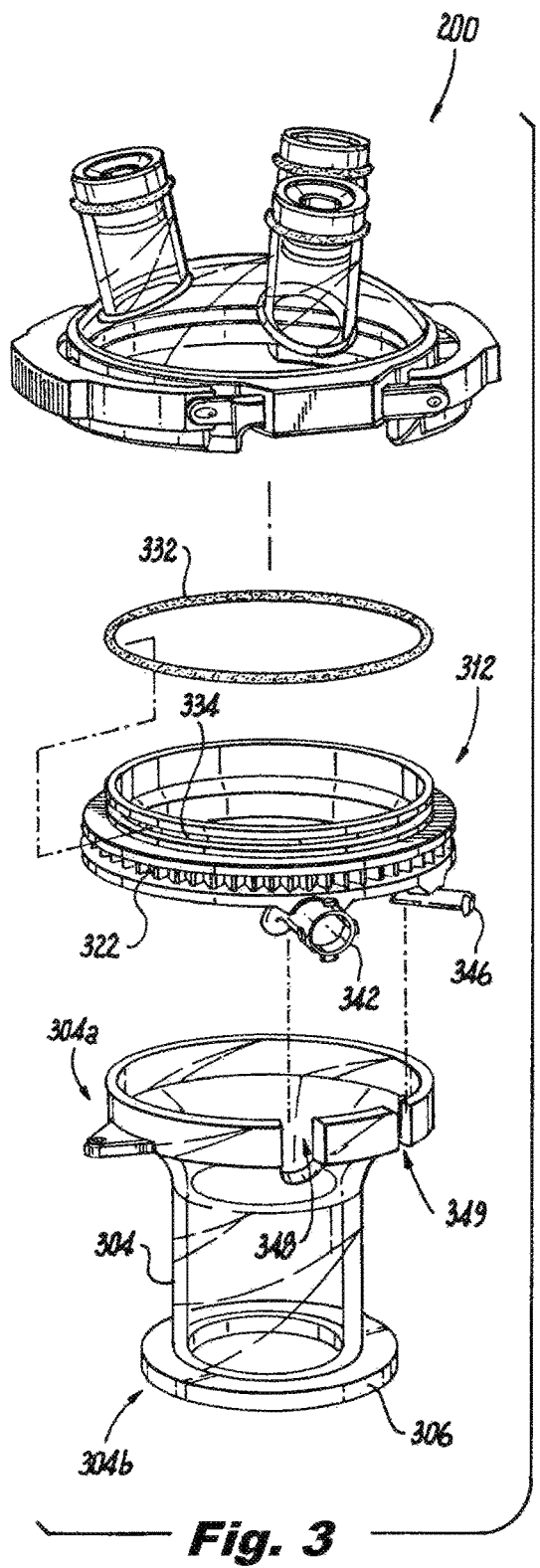
FIG. 3 is an exploded view of the multi-port access device, showing an O-ring and a retaining ring.
Figure 4:
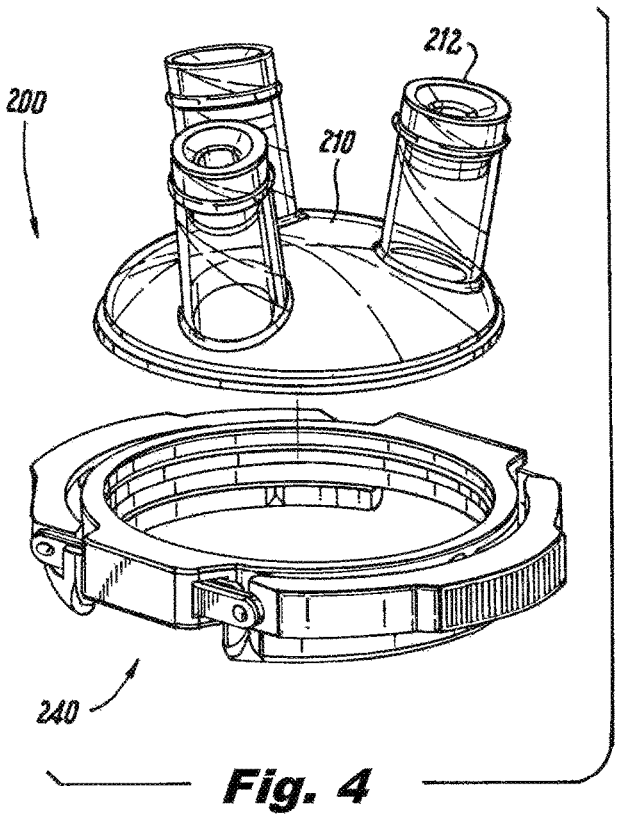
FIG. 4 is an exploded view of the multi-port sub assembly showing access ports and a latch assembly
Figure 5:
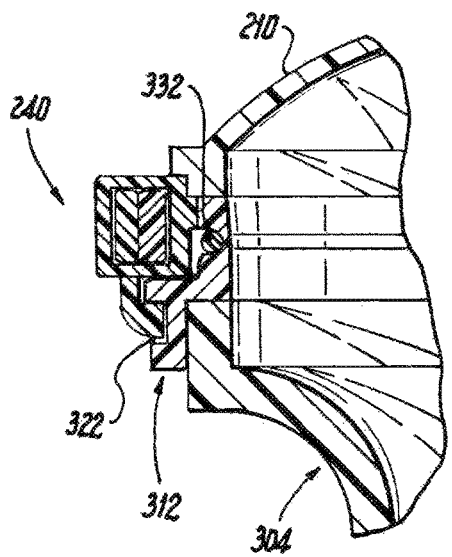
FIG. 5 is a cross-sectional view taken along line 5-5 of FIG. 1, showing ratchet teeth of the latch assembly engaged with the retaining ring.

The multi-port assembly 200 is comprised of an elastic access portion 210 and a latch assembly 240 (shown best in FIG. 4). The elastic access portion 210 is generally dome shaped and includes a plurality of access ports 212 for insertion of surgical instruments therethrough 104. The latch assembly 240 couples the multi-port assembly 200 to a ratchet ring 312 (shown in FIG. 3) of the wound protector assembly 300.

Figure 6:
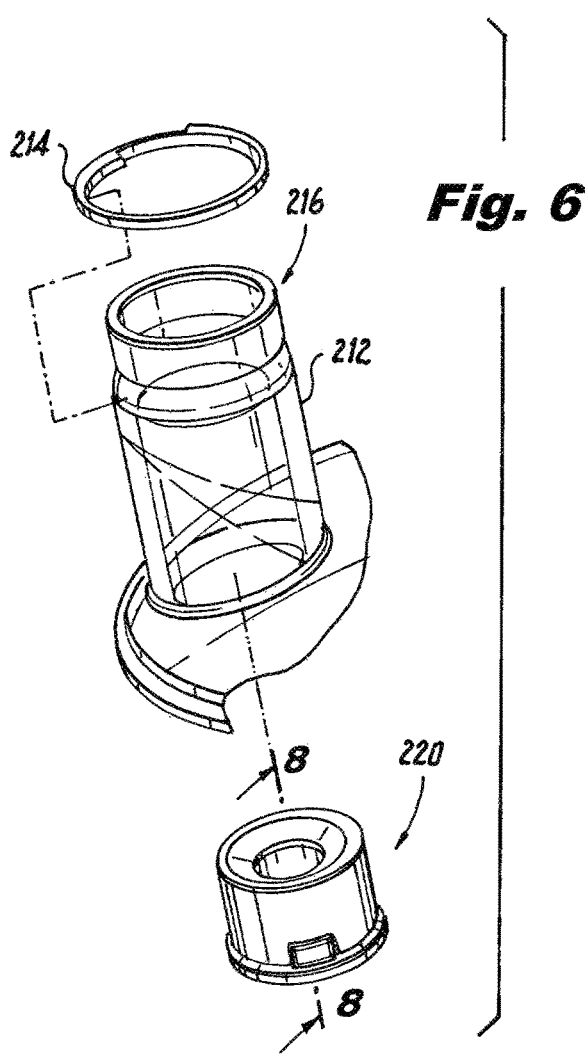
FIG. 6 is an exploded view of a single access port of the multi-port sub assembly, showing a seal assembly therein.
Figure 7:
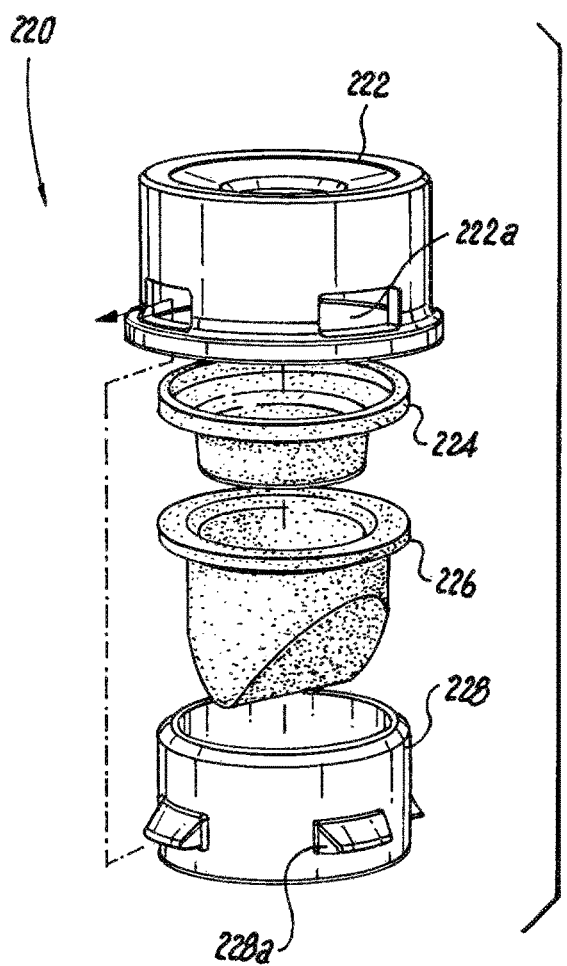
FIG. 7 is an exploded view of the seal assembly, showing a main seal and a duck bill seal.
Figure 8:
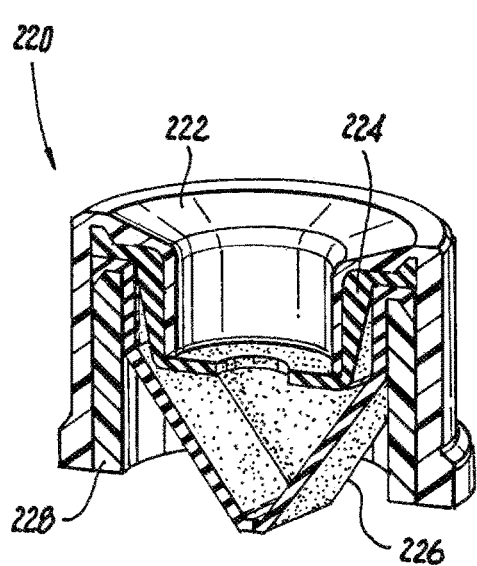
FIG. 8 is a cross-sectional view taken along line 8-8 of FIG. 6, showing alignment of the main seal and duck bill seal.
Figure 9:
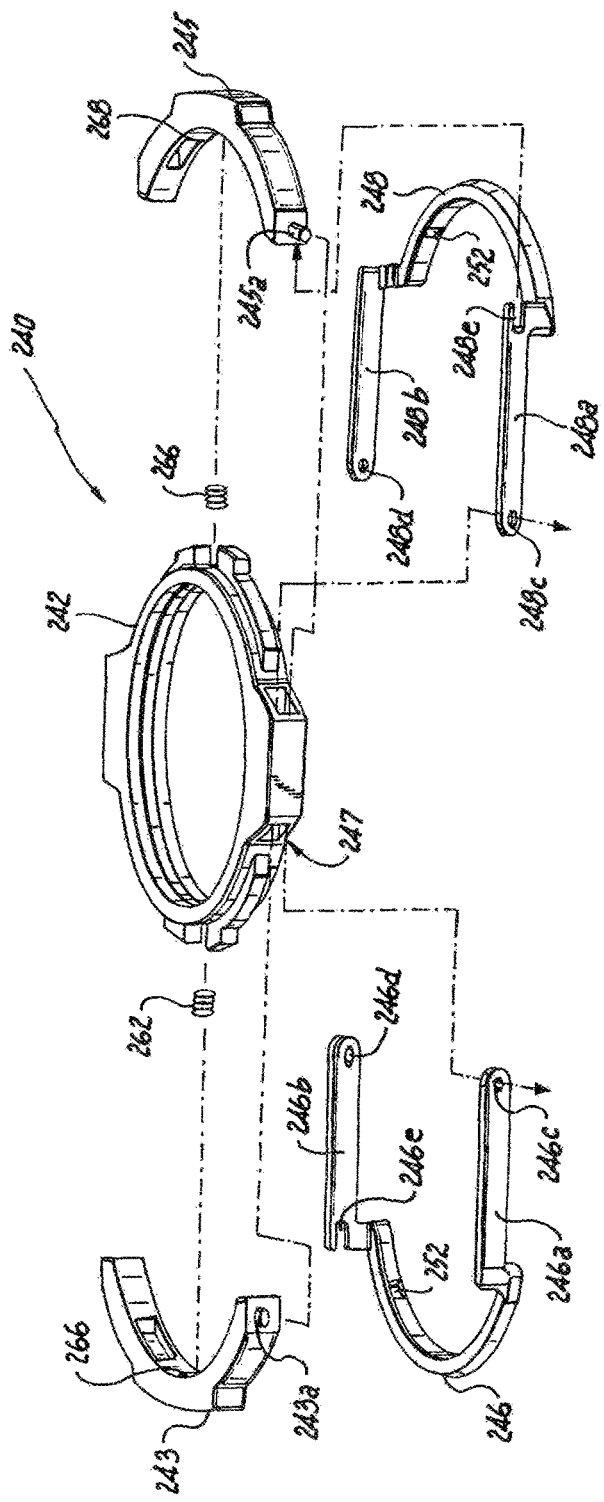
FIG. 9 is an exploded view of the latch assembly of the multi-port sub assembly, showing a coupler body and symmetrical latches.
Figure 11:
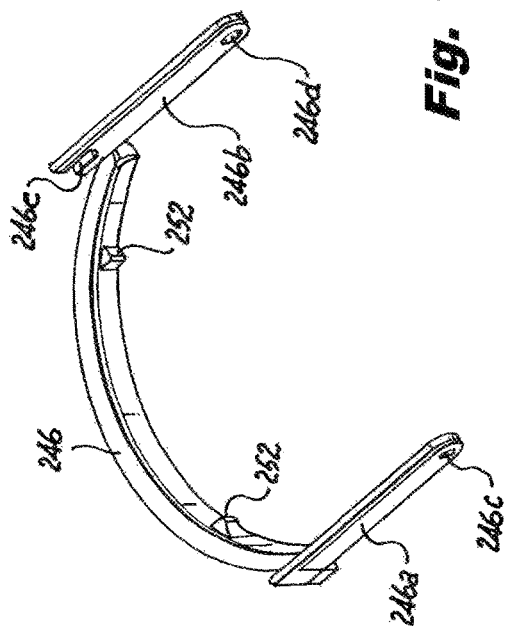
FIG. 11 is a perspective view of a latch of the latch assemblies, showing ratchet teeth.
Figure 10:
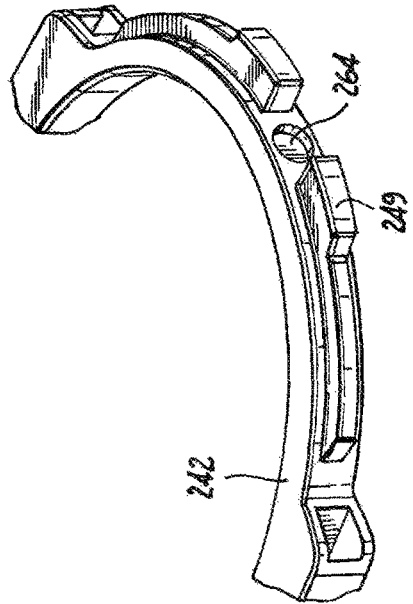
FIG. 10 is a perspective view of a portion of the coupler body, showing spring pockets and through slots.

Referring to FIGS. 6-8, each access port 212 of the elastic access portion 210 includes a seal assembly 220 and a retaining feature 214 for maintaining the seal assembly 220 in position. As shown in FIG. 7, the seal assembly 220 includes a top 222 which encloses a main seal 224 and a duck bill seal 226 between the top 222 and a bottom ring 228. The top 222 and the bottom ring 228 are press fit together when tabs 228a of the bottom ring 228 are inserted into openings 222a of the top 222. Each seal assembly 220 is inserted into a tip 216 of the respective access port 212. The retaining feature 214 is positioned on an external surface of the tip 216 to compress the tip 216 onto the seal assembly 220 and prevent movement.

Figure 12:
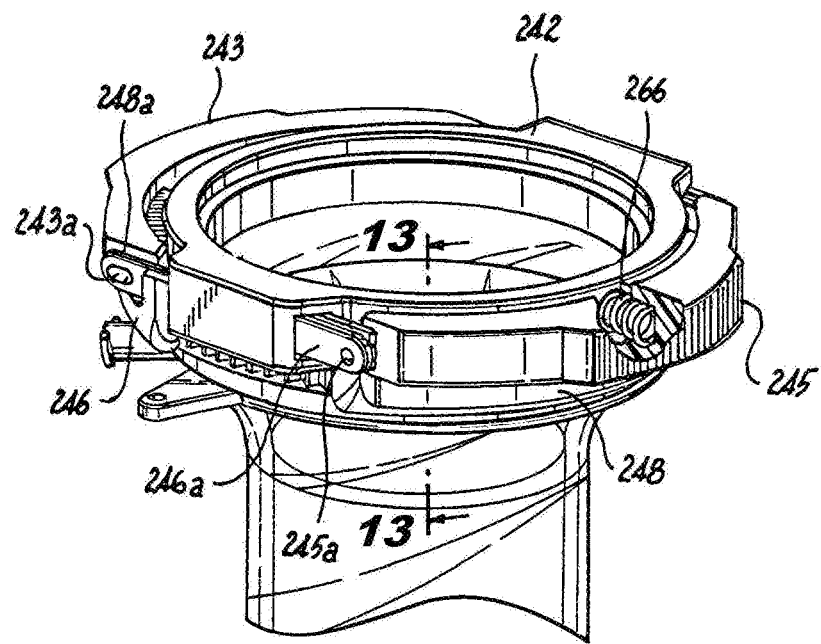
FIG. 12 is a perspective view of an assembled wound protector sub assembly, showing a spring within the latch assembly in a compressed position.

With reference to FIGS. 9-15, the latch assembly 240 of the multi-port assembly 200 is shown. The latch assembly 340 includes a circular coupler body 242 and two symmetrical latches 246, 248 with buttons 243, 245, respectively. The latches 246, 248 are generally semi-circular with parallel extensions 246a, 246b, 248a, 248b configured to slideably engage with slots 247 of coupler body 242. Each extension 246a, 246b, 248a, 248b includes a hole 246c 246d, 248c, 248d which engages a post 243a, 245a on the button 243, 245 of the opposing latch. For example, as best seen in FIG. 12, hole 246a of extension 246 engages post 245a of button 245.

In addition, at least one extension 246a, 248a of each latch 246, 248 includes a notch 246e, 248e (shown in FIG. 11) to engage corresponding post of button 243, 245 such that button 243, 245 securely fits to latch 246, 248. Further, coupler body 242 includes ribs 249 (shown in FIG. 10) to help maintain positioning of button 243, 245.

Each latch 246, 248 further includes ratchet teeth 252 (shown in FIG. 11) to mate with the ratchet ring 312 of the wound protector assembly. Two springs 262, 266 (shown best in FIG. 9) are disposed within spring pockets 264, 268 between the body 242 and a respective button 243, 245 for releasing the latch assembly 246, 248 from the ratchet ring 312. More specifically, compression of the springs 262, 266 manipulates extensions 246a, 246b, 248a, 248b and flexes ratchet teeth 252 to lock or release from the ratchet ring 312.

The ratchet ring 312 includes a plurality of circumferentially arranged ratchet teeth 322 to mate with ratchet teeth 252 of the latch assemblies 240. An O-ring 332 is positioned within an annular groove 334 of the ratchet ring to seal and secure the multi-port assembly 200 to the wound assembly 300. Ports 342, 346 for the air seal line 106 and sensing line 108 extend from the ratchet ring 312 and secure into openings 348, 349 of the wound protector assembly 300.

As best shown in FIG. 3, the wound protector assembly 300 includes an elastic wound protector body 304 extending downwardly from the ratchet ring 312. The wound protector 304 includes at least one tie down feature 352 at the proximal end 304a for securing the access device 100 during a surgical procedure. A flange 306 extends from a distal end 304b of the wound protector 304 to secure the wound protector 304 within the opening of the patient.

Figure 13:
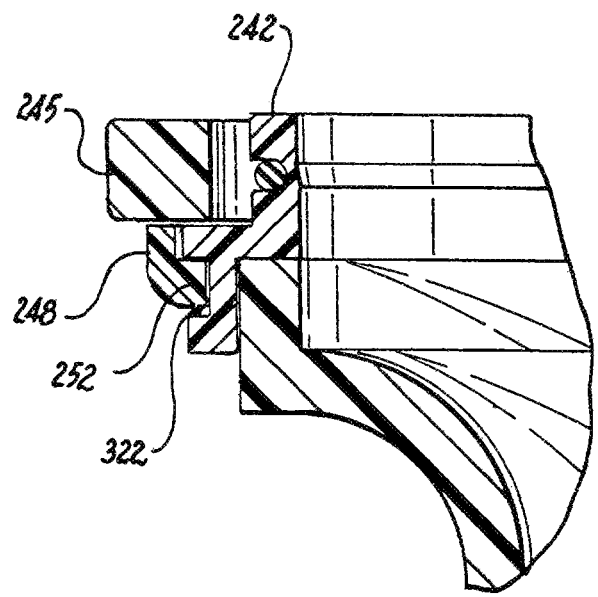
FIG. 13 is a cross-sectional view taken along line 13-13 of FIG. 12, showing engagement of the ratchet teeth of the latch assembly and the retaining ring when the spring is in an uncompressed position.

To assemble multi-port sub-assembly 200 to the wound protector sub-assembly 300 a user squeezes the buttons 243, 245 of the latch assembly 240. The multi-port sub assembly 200 is pressed down and over the O-ring 332 and ratchet ring 312 until the ratchet teeth 252 on the latches 246, 248 are aligned with corresponding ratchet teeth 322 of the ratchet ring 312. Referring to FIG. 13, releasing the buttons 243, 245 allows the ratchet teeth 252 to lock into the ratchet ring 312.

Figure 14:
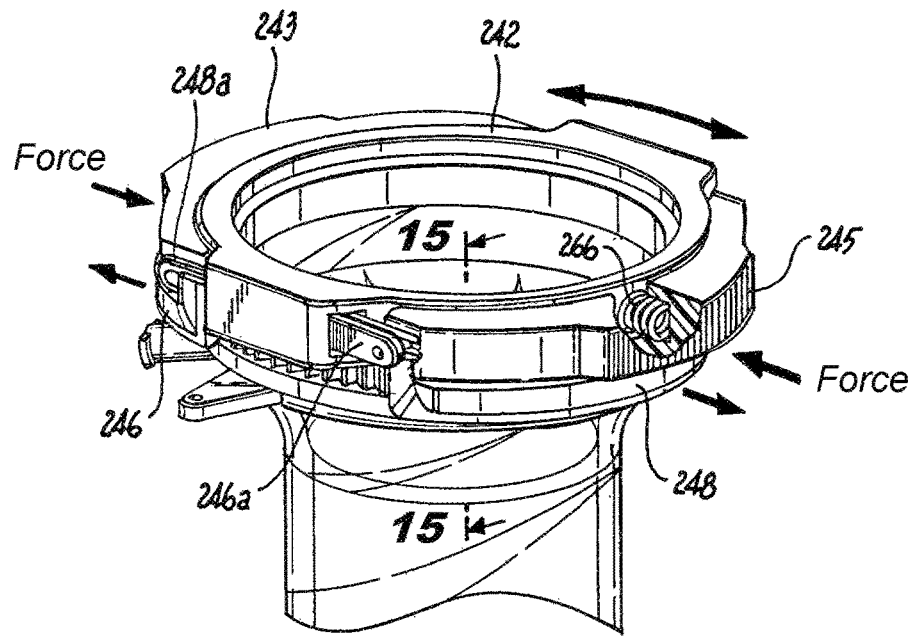
FIG. 14 is a perspective view of the wound protector sub assembly, showing rotation of the locking ring.
Figure 15:
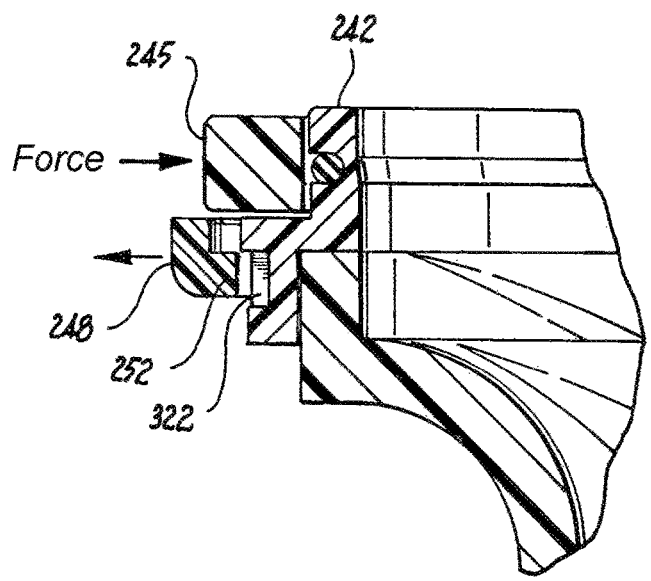
FIG. 15 is a cross-sectional view taken along line 12-12 of FIG. 11, showing pressure on a button of the latch assembly releases ratchet teeth from retaining ring.

As shown best in FIGS. 14 and 15, to rotate the multi-port assembly 200, the user again squeezes the buttons 243, 245 to release the ratchet teeth 252 from ratchet ring 312 (shown in FIG. 13) and then rotates (shown in FIG. 12) the multi-port assembly 200 until the desired position of access ports 212 is reached. Once the desired position is reached, releasing the buttons 243, 245 will again lock ratchet teeth 252 with ratchet teeth 332 and secure the multi-port assembly 200 in position for use.

Figure 16:
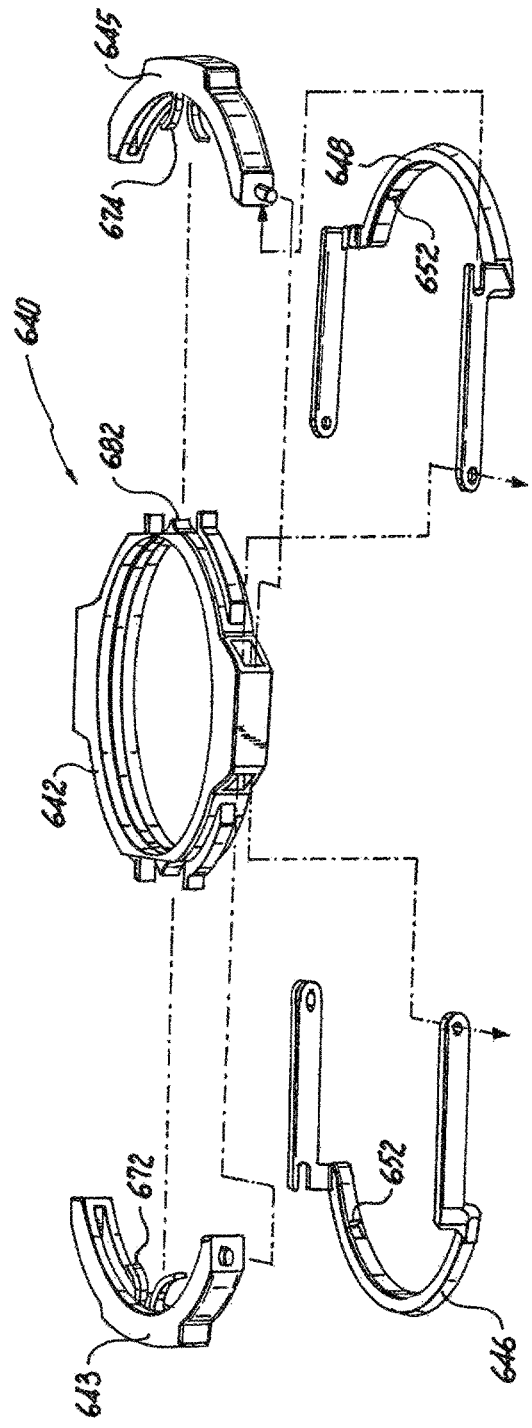
FIG. 16 is an exploded view of an alternate embodiment of a latch assembly, showing flexible tabs.
Figure 17:
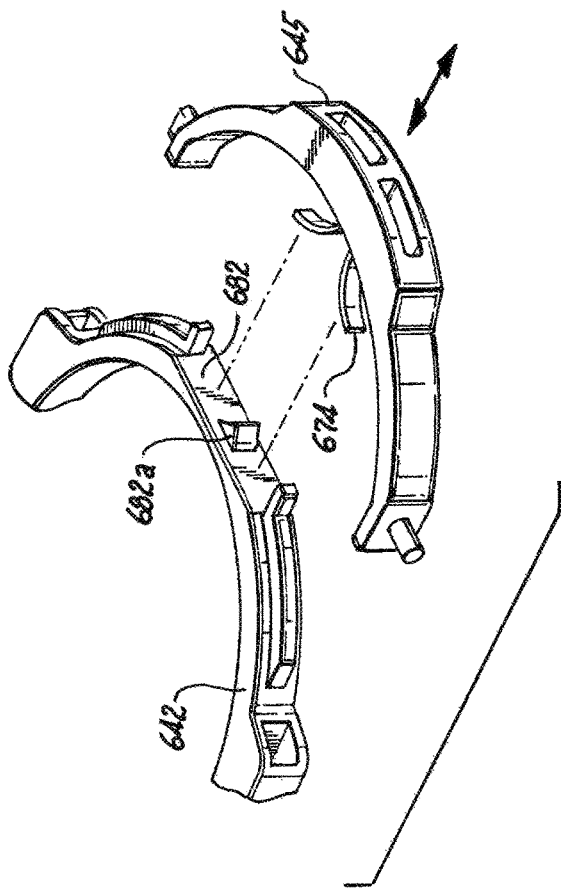
FIG. 17 is an exploded view a portion of the latch assembly of FIG. 16, showing flexible tabs aligned with a flat face of coupler body.

With reference to FIGS. 16 and 17, an alternate embodiment of a latch assembly 640 is shown. Latch assembly 640 can be used in a similar manner as latch assembly 240 with multi-port assembly 200 and wound protector assembly 300.

Latch assembly 640 includes latches 646, 648 and buttons 643, 645, however springs are replaced with flexible tabs 672, 674. More specifically, flexible tabs 672, 674 having a generally "V" shape extend from buttons 643, 645. Flexible tabs 672, 674 mate with a flat face 682 on coupler body 642 when buttons 643, 645 are pressed. Flexible tabs 672, 674 operate in a similar manner as springs 262, 266 in that pressure on buttons 643, 645, compresses flexible tabs 672, 674 to release or lock ratchet teeth 652 to ratchet ring 312.

Figure 18:
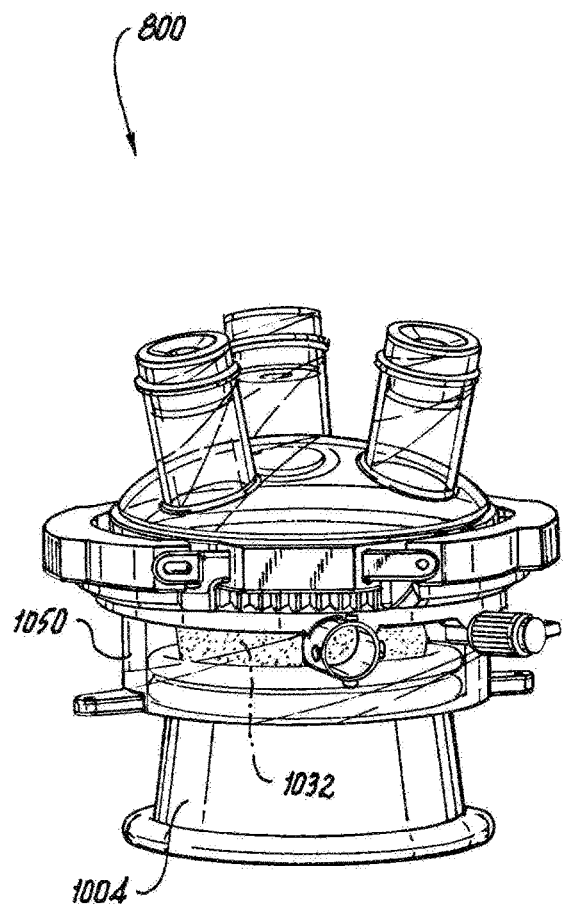
FIG. 18 shows an embodiment of the multi-port access device of the subject invention for connecting the multi-port sub assembly to a wound protector sub assembly for use in laparoscopic surgical procedures.
Figure 19:
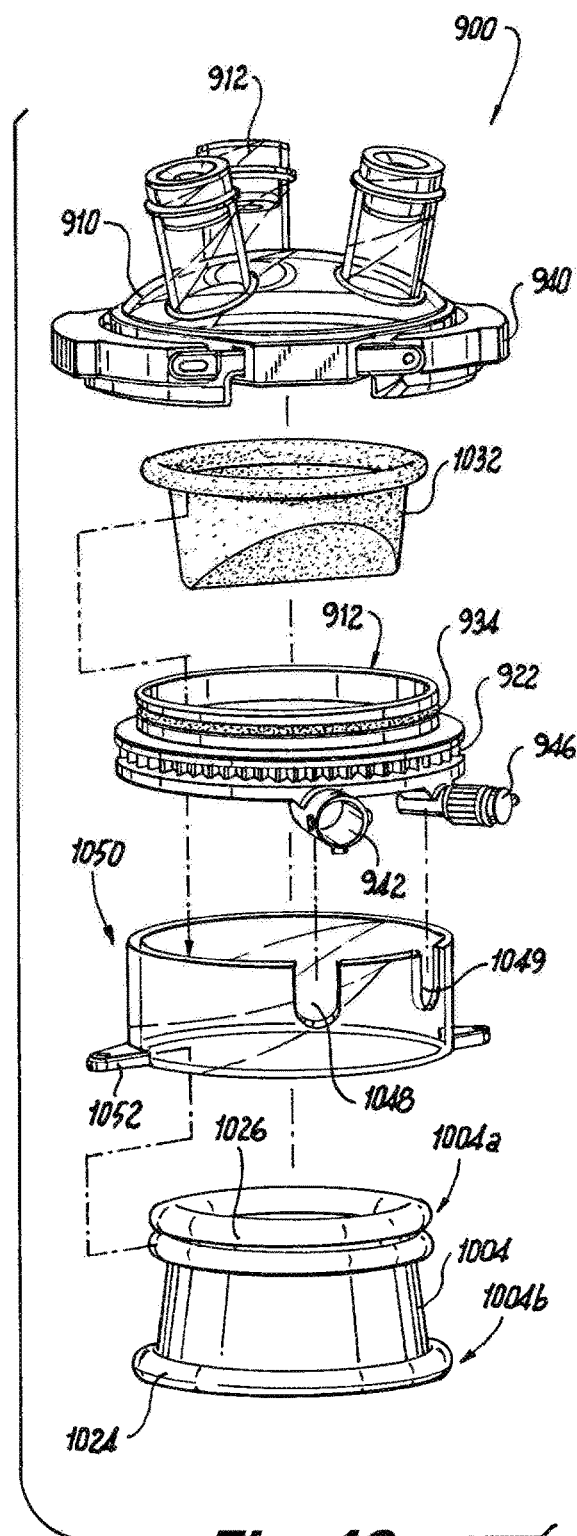
FIG. 19 is an exploded view of the multi-port access device of FIG. 18, showing a seal.

FIGS. 18 and 19 illustrate an alternate embodiment of a multi-port access device 800 preferably for use during laparoscopic procedures. The multi-port assembly 900 is similar to multi-port assembly 200 having an elastic access portion 910 with a plurality of access ports 912 and a latch assembly 940. In addition, retaining ring 912 is similar to retaining ring 312 having an O-ring seal 934, ratchet teeth 922 and ports for air seal 942 and pressure sensing 946.

In this embodiment, wound protector 1004 includes a bottom lip 1024 around a distal end 1004b. At least one top lip 1026 surrounds a proximal end 1004a to secure an adaptor 1049 (best seen in FIG. 19) to wound protector 1004. Adaptor 1049 is generally ring-shaped that fits over top lip 1026 and includes openings for 1048, 1049 for ports 942 and 946, respectively. Adaptor 1049 also includes suture tie downs 1052 similar to suture tie downs 352. A duck bill seal 1032 mates with the adaptor 1049 and the wound protector 1004.

To assemble, the wound protector 1004 is first inserted into an opening of a patient. The adaptor 1049 is pressed down and over lip 1026 of the wound protector 1004. Retaining ring 912 is positioned on top of adaptor 1049 with ports 942, 946 in openings 1048, 1049, respectively. Duck bill seal 1032 is next fit into retaining ring 912 and adaptor 1049 and multi-port assembly 900 is attached to retaining ring 912 in the same manner as multi-port assembly 200 and retaining ring 312.

Figure 20:
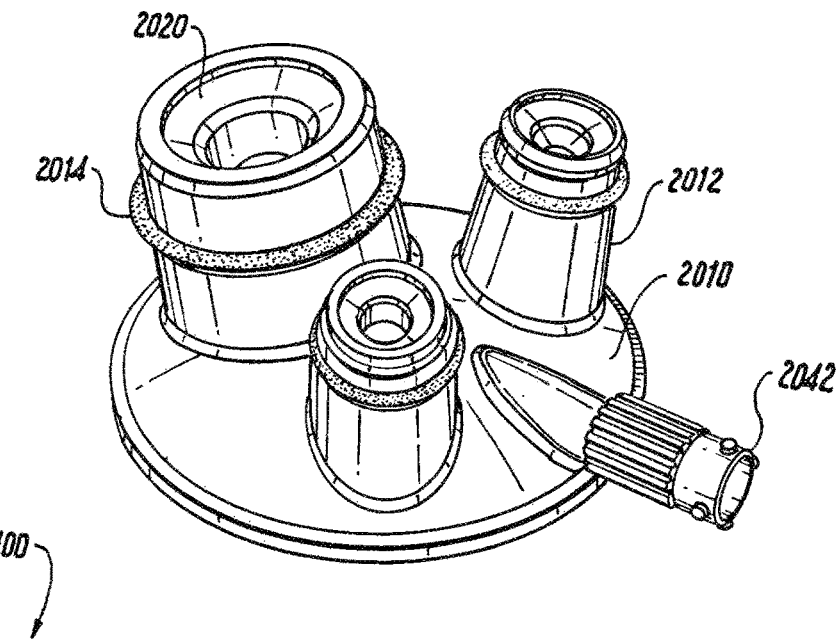
FIG. 20 is a perspective view of an alternate embodiment of an elastic access portion of the multi-port sub assembly, showing access ports of varying sizes.

FIG. 20 illustrates an alternate embodiment of an elastic access portion 2010 for use in the multi-port assembly 200. Access ports 2012 and seal assemblies 2020 with retaining rings 2014 are shown in various dimensions. For example, 12 mm, 10 mm, 8 mm, and 5 mm access ports 2012 can be used. Potential use of even smaller ports (3 mm) is also envisioned. In this embodiment, an air seal port 2042 is also part of the elastic access portion 2010.

Figure 21:
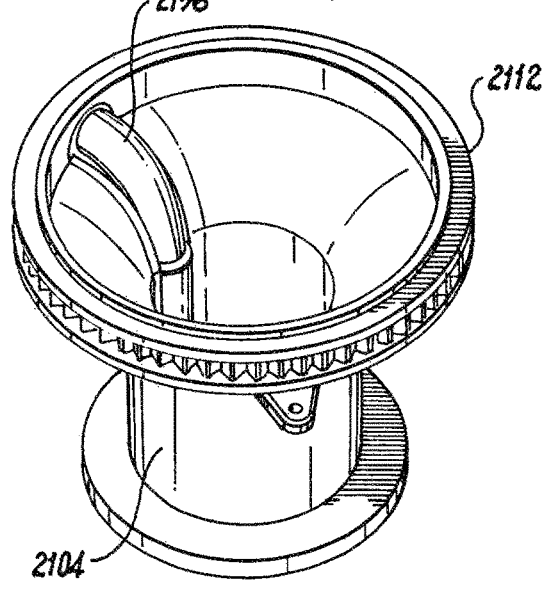
FIG. 21 is a perspective view of an alternate embodiment of a wound protector sub assembly showing a lumen molded therein.
Figure 22:
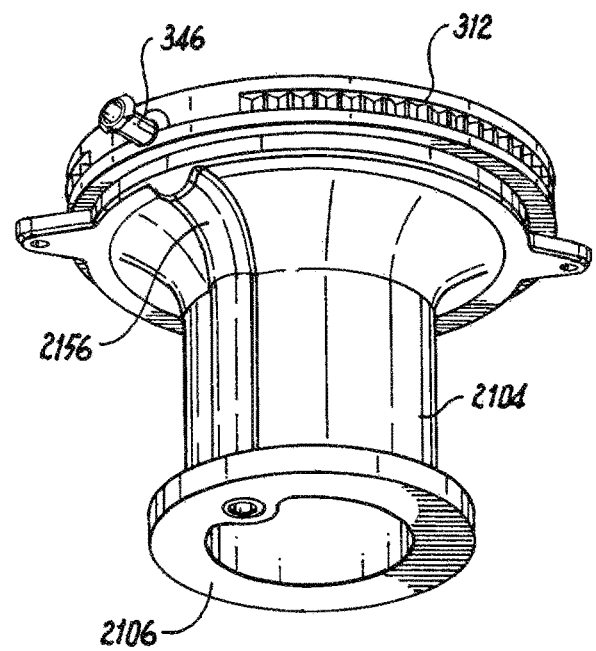
FIG. 22 is a perspective view of the wound protector of FIG. 21, showing the lumen extending through the wound protector body.
Figure 32:
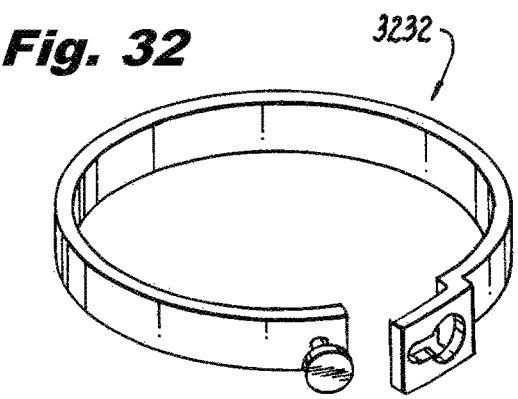
FIG. 32 is a perspective view of an alternate embodiment of a belt closure for the access port, showing a pin and key.
Figure 33:
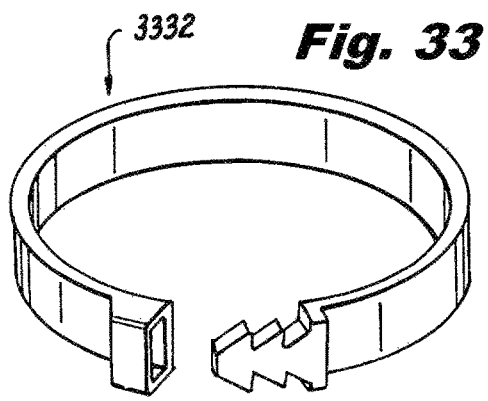
FIG. 33 is a perspective view of an alternate embodiment of a belt closure for the access port, showing a graduated ratchet.

FIGS. 21 and 22 show an alternate embodiment of a wound protector 2100 for use with retaining ring 312. A lumen 2156 is molded into the wound protector body 2104 which connects from the sensing port 346 to the flange 2106 of the wound protector 2104. This embodiment can potentially enhance smoke evacuation by increasing the distance between the sensing line 346 and air seal line 342.

FIGS. 23-28 show alternate embodiments for seal assemblies 2320 and 2620 within access ports 2312 and 2612, respectively. Similar to access port 220, access port 2320 and 2620 include main seals 2324 and 2624 and duck bill seals 2326 and 2626 between tops 2322 and 2622 and bottom rings 2328 and 2628, respectively. With reference to FIGS. 23-25, bottom ring includes a proud ring feature 2328a (shown in FIG. 24) which engages an internal groove 2322a of top 2322 (shown in FIG. 25). In this embodiment, the top 2322 and bottom ring 2328 are press fit together and hold the main seal 2324 and duckbill 2326 seal together. With reference to FIGS. 26-28, top 2622 includes flexible tabs 2622a which engage slots 2628a on the bottom ring 2628. Once the flexible tabs 2622a are press fit into the slots 2628a, the flex tabs 2622a will lock in place and hold the main seal 2624 and duckbill 2626 seal together.

FIG. 29 shows an alternate embodiment for a retaining feature for maintaining seal assembly 220 within access ports 212 of the elastic access portion 210 utilizing a spring hose clamp 2932. The clamp 2932 is held in position and operated with an inner ring 2934 and outer ring 2936. The inner ring 2934 holds one end 2932a of the clamp 2932 and another end 2932b of the clamp 2932 is held by the outer ring 2936. Rotating the outer ring 2936 and inner ring 2934 in opposing directions will open and close the clamp 2932 and allow for adjustability.

FIG. 30 shows another embodiment of a retaining feature 3032 wherein a living hinge 3034 is included in a 3032. The retaining feature 3032 has ratchet teeth 3042 that mate with opposing ratchet teeth 3046 of the ring 3032 and that once wrapped around an access port 220 will ratchet closed.

FIG. 31 shows yet another embodiment for the retaining feature including a strap or belt 3132 that could be used to hold access port 220 within the opening 212. In this embodiment, outward extending pins 3132a mate with holes 3132b of opposing ends of strap to secure 3132 the strap together.

Figure 34:
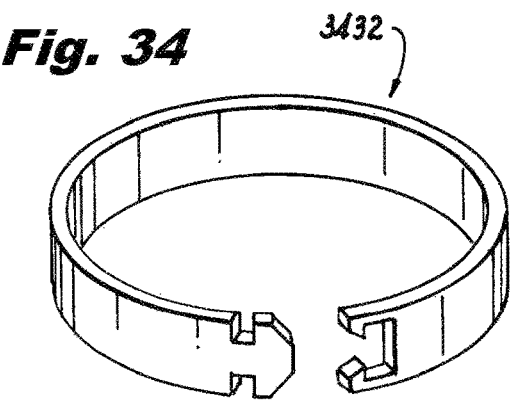
FIG. 34 is a perspective view of an alternate embodiment of a belt closure for the access port, showing a hook and lock.
Figure 35:
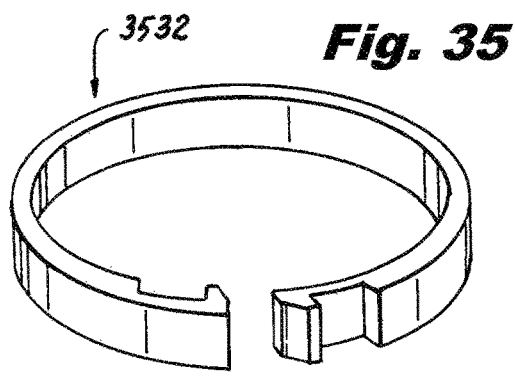
FIG. 35 is a perspective view of an alternate embodiment of a belt closure for the access port, showing a hook and lock.
Figure 36:
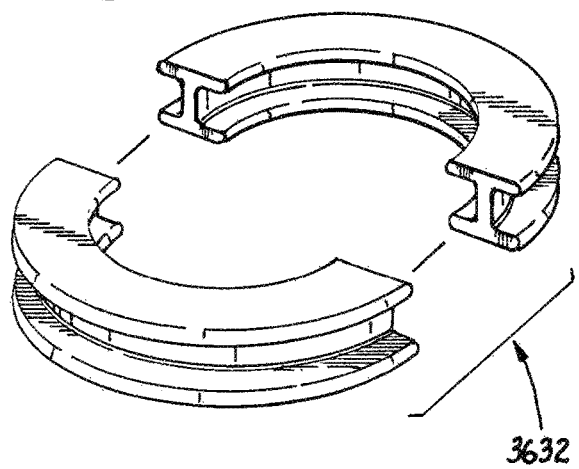
FIG. 36 is a perspective view of an alternate embodiment of a belt closure for the access port, showing I-beams.
Figure 37:
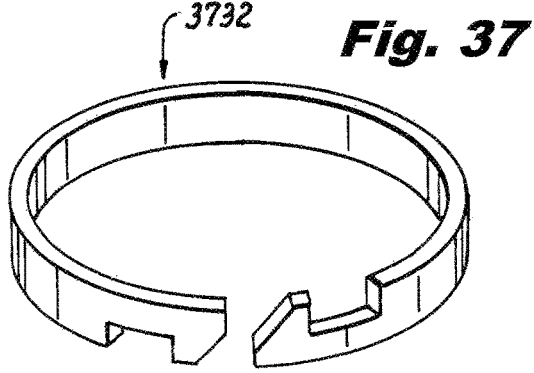
FIG. 37 a perspective view of is an alternate embodiment of a belt closure for the access port, showing a hook and lock.
Figure 38:
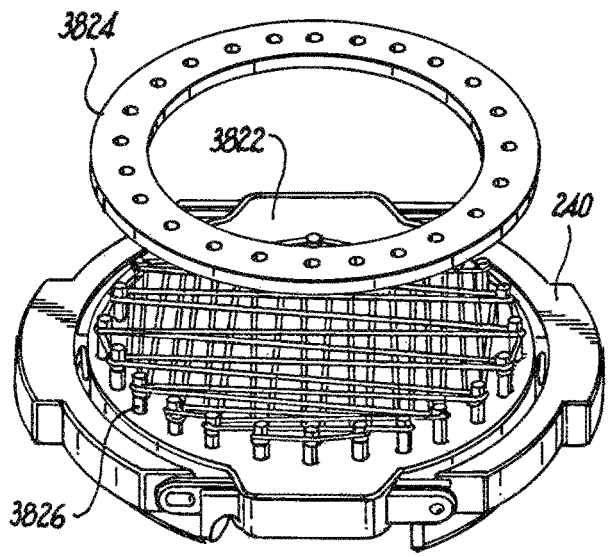
FIG. 38 is an exploded view of an alternate embodiment a multi-port sub assembly, showing a weave layer.

FIGS. 32-37 show varying embodiments of locking mechanisms for straps 3232, 3332, 3432, 3532, 3632, 3732. Strap 3232 includes a pin configured to be inserted and slid through slot to lock strap into position. Strap 3332 includes a pull and twist design which allows for tightening the strap as needed to hold seal assembly in position. FIG. 34 illustrates strap 3432 having one generally arrow shaped end that can be inserted into an opening at an opposing end by press fitting the ends together. FIGS. 35 and 37 illustrate straps 3532 and 3732 each having hook features with varying orientations. Strap 3632, shown in FIG. 36, includes I-beams on opposing ends that snap fit together.

With reference to FIGS. 38-42 alternate designs to the multi-port sub assembly 200 are shown by incorporating stitching underneath the access ports 212. When assembled the stitching is enclosed within the latch assembly 240. The stitching includes elastic stitches 3828 in an alternating pattern, a continuous stitch, or multiple layers with alternating gaps.

Figure 39:
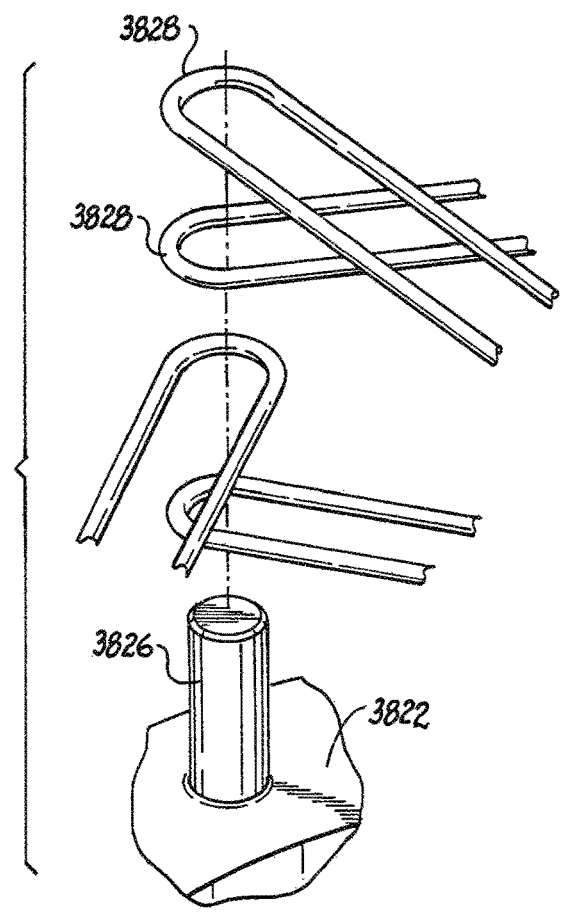
FIG. 39 is an exploded perspective view showing the weave layer of FIG. 38 in an alternating pattern.
Figure 40:
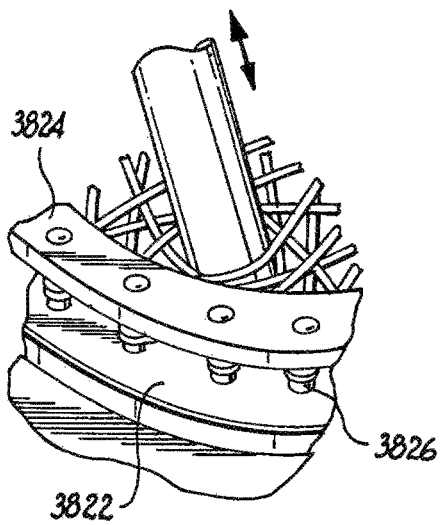
FIG. 40 is a perspective view showing a surgical instrument inserted through the weave layer of FIG. 38.

More specifically, as shown in FIG. 39 each individual elastic string 3828 overlaps in an alternating pattern such that there are no openings or leaks. As best seen in FIG. 40, this embodiment includes a circular bottom plate 3822, a top ring plate 3824 and a plurality of posts 3826 along the circumference of the bottom plate 3822 for looping each stitch 3828 around. This design can include one more than one layer of weaving to compensate for "cat-eyeing".

Figure 41:
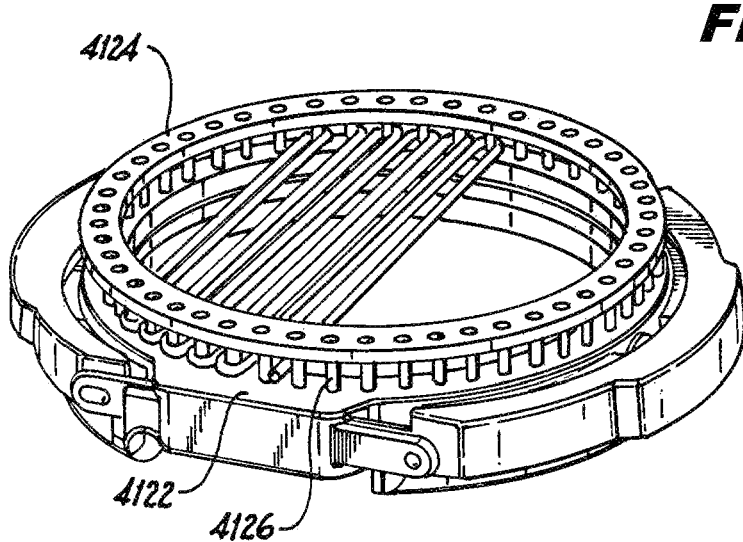
FIG. 41 is a perspective view of an alternate embodiment of a multi-port sub assembly, showing a parallel stitch design.
Figure 42:
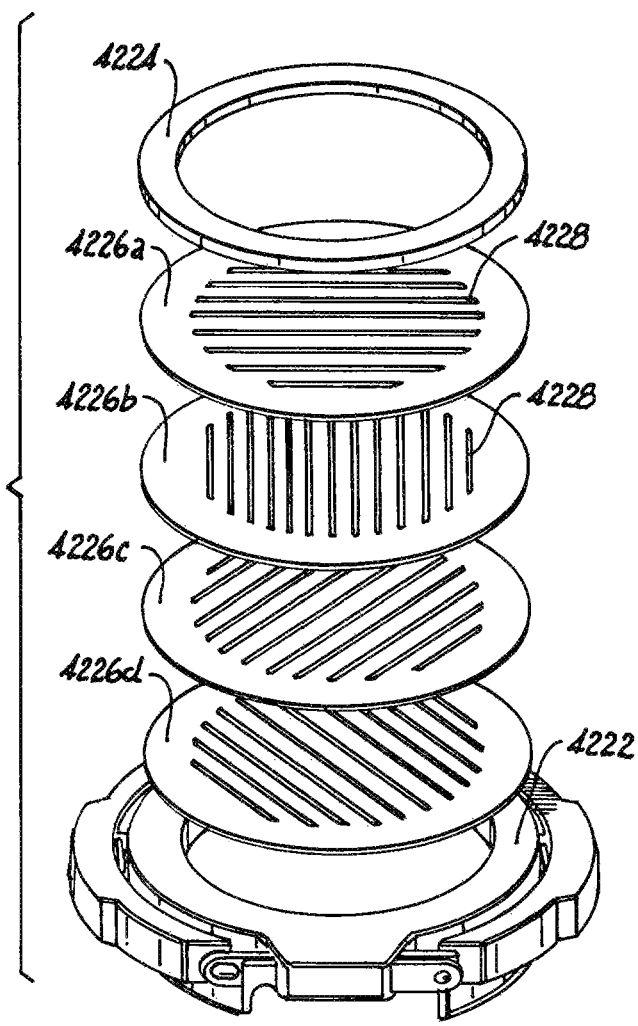
FIG. 42 is an exploded perspective view of an alternate embodiment of a multi-port sub assembly, showing a stitch design with multiple layers.
Figure 43:
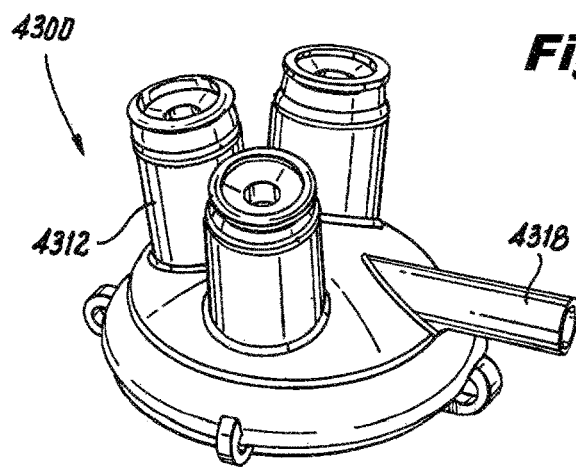
FIG. 43 is a perspective view of an alternate embodiment of a multi-port sub assembly, showing a vacuum port.
Figure 44:
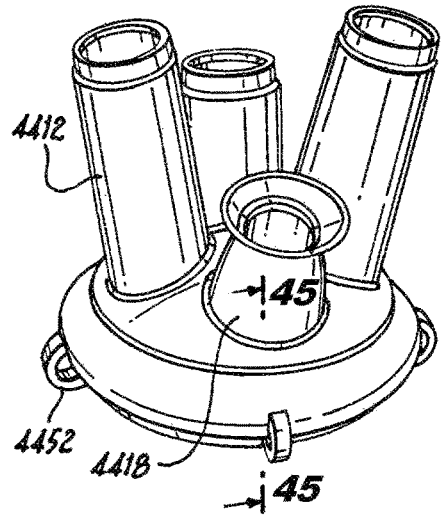
FIG. 44 is a perspective view of an alternate embodiment of a multi-port sub assembly, showing ports of varying lengths.
Figure 46:
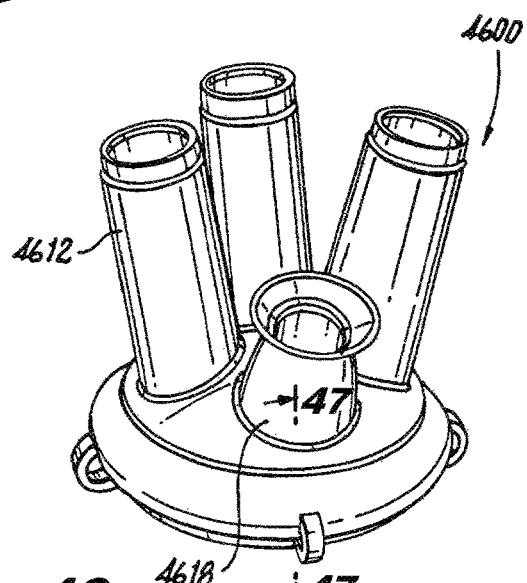
FIG. 46 is a perspective view of an alternate embodiment of a multi-port sub assembly, showing a trocar port.

FIG. 41 shows a continuous elastic stitch 4128 design that would be wound in one direction around posts 4126 between a bottom plate 4122 and a top ring 4124. FIG. 42 shows a plurality of circular elastic layers 4226a-d where elongated gaps 4228 on each layer 4226a-d are angled with each adjacent layer 4226a-d. In this embodiment, each layer 4226a-d is manufactured the same, but assembled in different orientations (0, 45, 90, 135 degrees). Regardless of the embodiment, a user inserts surgical instruments through the weave, stitch, or layers to maintain stability of the surgical instruments during a surgical procedure.

Referring now to FIGS. 43-47 alternate embodiments of a multi-port assembly are shown. Various combinations in the numbers of access ports, the heights, and different combinations of access ports and trocar ports are contemplated. For example, multi-port sub assembly 4300 (shown in FIG. 43) includes access ports 4312 with equal heights and a pressure/vacuum port 4318. Multi-port assembly 4400 (shown in FIG. 44) includes access ports 4412 of varying heights and a trocar port 4418 and multi-port assembly 4600 (shown in FIG. 46) includes access ports 4612 and a trocar port 4618.

Figure 45:
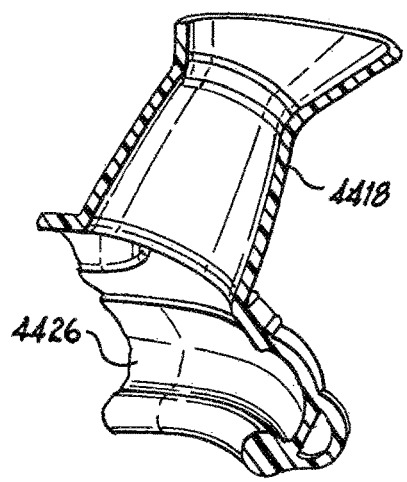
FIG. 45 is a cross-sectional view taken along line 45-45 of FIG. 44, showing a groove to engage a wound protector sub assembly.
Figure 47:
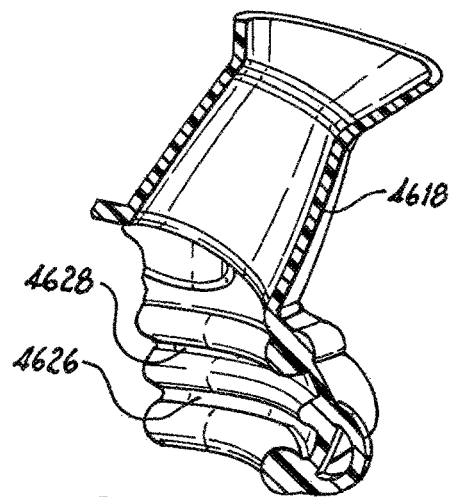
FIG. 47 is a cross-sectional view taken along line 47-47 of FIG. 46, showing a plurality of grooves to engage a wound protector sub assembly.

FIGS. 45 and 47 also show alternate embodiments of attaching the multi-port assemblies 4300, 4400 and 4600 to a wound protector, for example, wound protector 1004 (shown in FIG. 19). Assemblies 4300, 4400 and 4600 include internal elastic features, for example grooves 4426, 4628 and 4626, which mate with at least one exterior ring, for example ring 1026, on the wound protector. The elastic feature seals the multi-port assembly to the wound protector.

Figure 48:
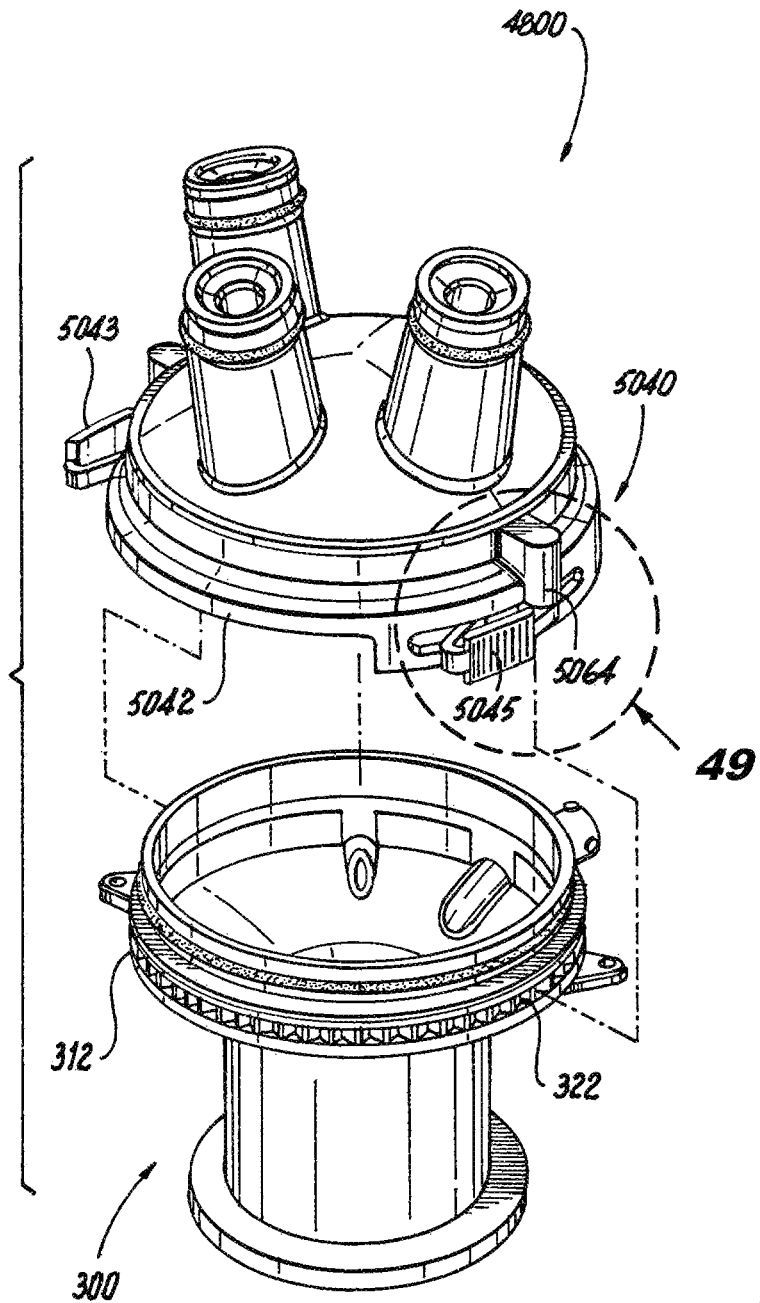
FIG. 48 is an exploded perspective view of an alternate embodiment of a latch assembly for the multi-port access device, showing spring loaded horizontal latches.
Figure 49:
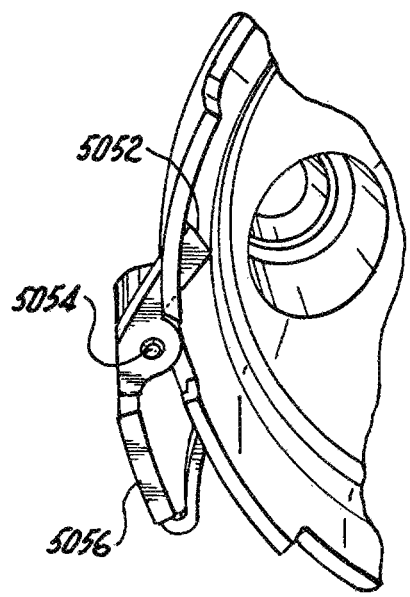
FIG. 49 is a detailed view of latches of FIG. 48, showing a flex arm and tab.
Figure 50:
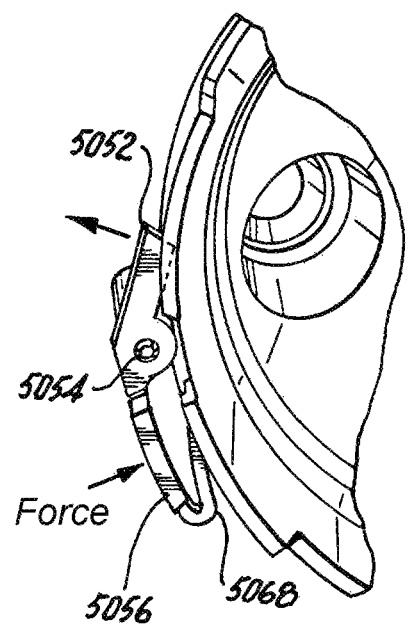
FIG. 50 is a detailed view of the latches of FIG. 48, show pressure on the flex arm releases tab.

FIGS. 48-50 show an alternate embodiment of a latch assembly 5140 for mating the multi-port assembly 4800 with the wound protector assembly 300. Multi-port assembly 2800 includes latch assembly 5040 having a coupler body 5042 with diametrically opposed horizontally aligned spring loaded latches 5043, 5045. Each latch 5043, 5045 has a ratchet tooth 5052 at one end, a flexible arm 5056 on the opposing end and a middle portion 5054 therebetween to pivot around. The coupler body 5042 has two slots 5064 (only one shown in FIG. 49-51 for clarity) for inserting the ratchet tooth 5052 therein and a groove 5068 for the flexible arm 5056 to mate with.

To operate, a user squeezes flexible arm 5056 and pivots the latches 5043, 5045 outwardly such that ratchet teeth 5052 engage ratchet teeth 322 of retaining ring 312. This design also allows the user to reposition the multi-port sub-assembly 4800 rotationally without losing the seal in a similar manner as multi-port sub assembly 200, described in FIGS. 1-15.

Figure 51:
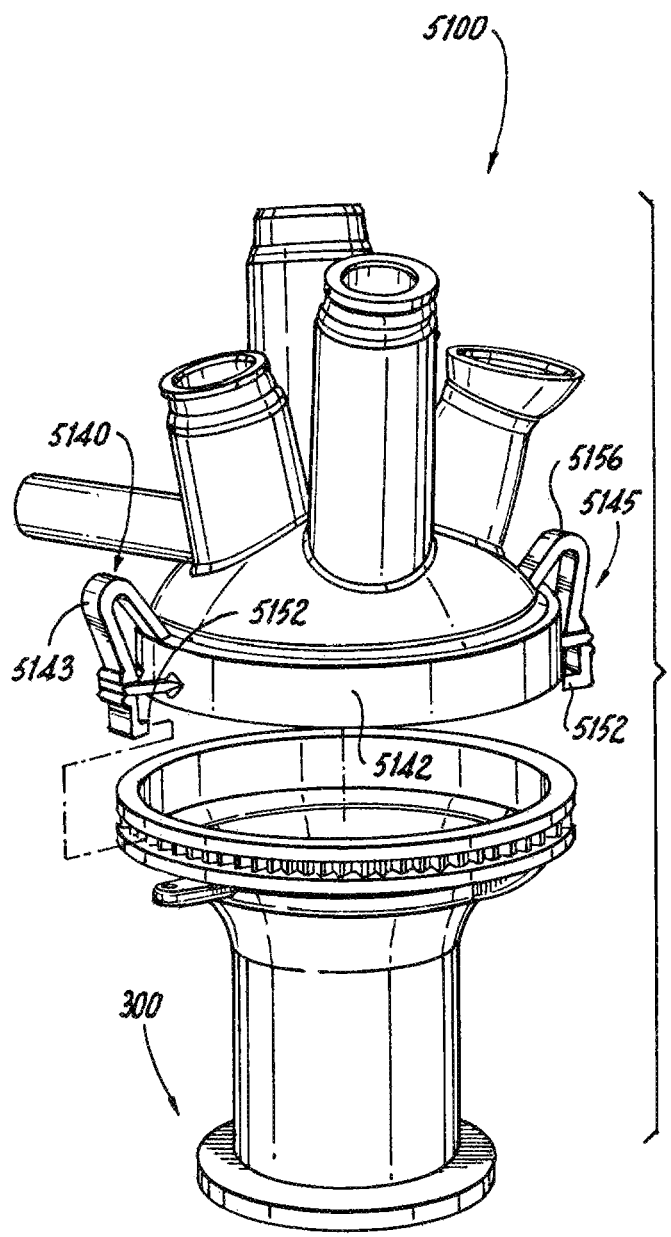
FIG. 51 is an exploded view of an alternate embodiment of a latch assembly for the multi-port access device, showing spring loaded vertical latches.
Figure 52:
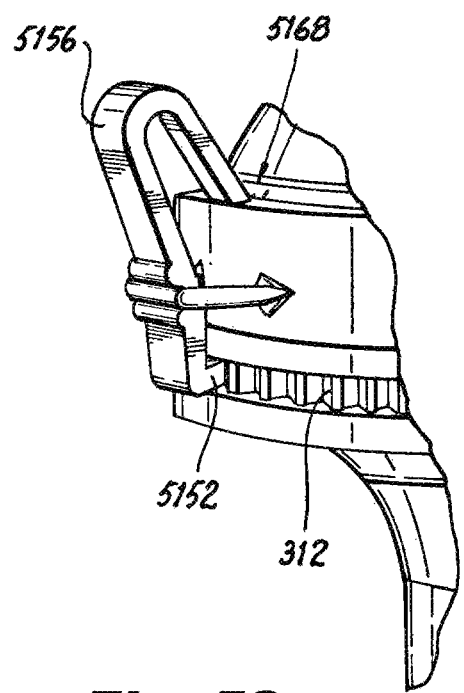
FIG. 52 is a perspective view of the latches of FIG. 51, showing a flex arm and hook.
Figure 53:
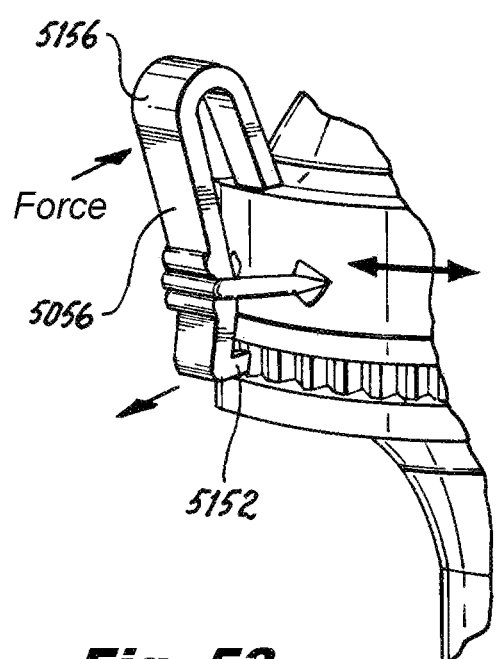
FIG. 53 is a perspective view of the latches of FIG. 51, show pressure on the flex arm releases hook.
Figure 63:
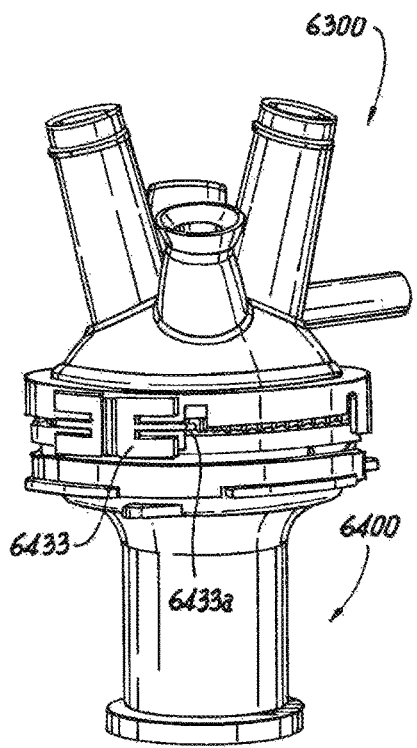
FIG. 63 is a perspective view of an alternate embodiment of a latch assembly for a multi-port access device, showing a spring loaded shroud.
Figure 64:
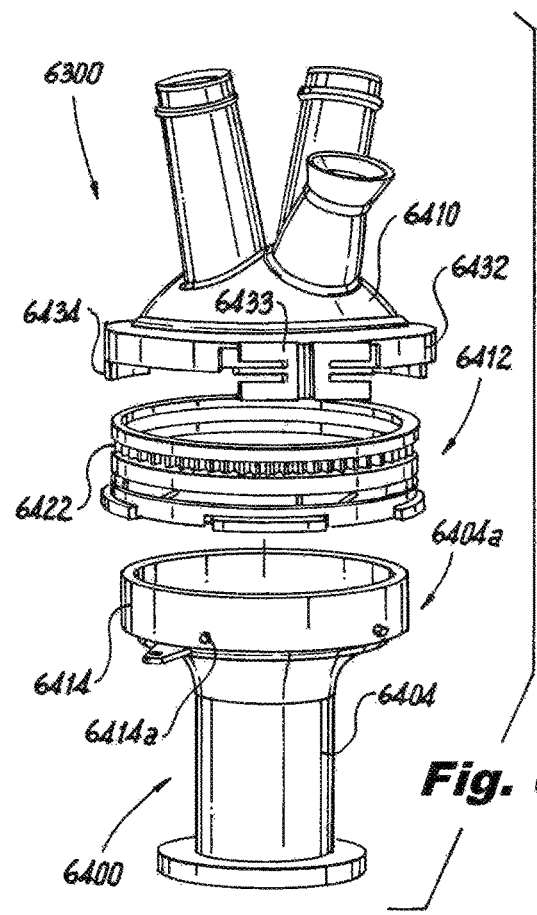
FIG. 64 is an exploded view of the multi-port access device of FIG. 63, showing alignment of the spring loaded shroud, retaining ring and wound protector body.
Figure 65:
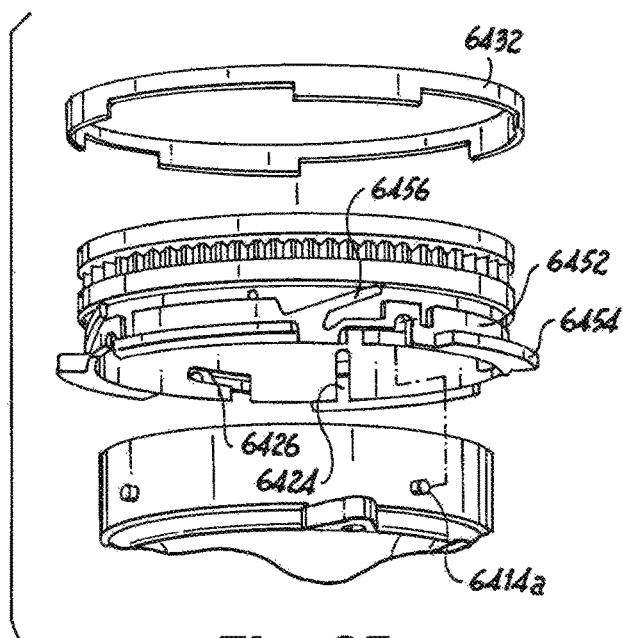
FIG. 65 is an exploded view of the shroud of FIG. 63, showing flex arms of the spring loaded shroud.
Figure 66:
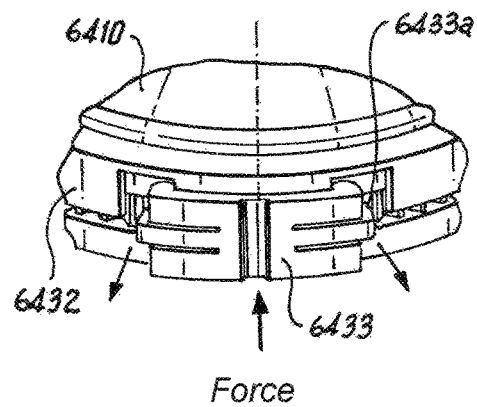
FIG. 66 is a perspective view of the shroud of FIG. 64, showing compression of the flex features.

FIGS. 51-53 illustrate yet another alternate embodiment of a latch assembly 5140 for mating multi-port assembly 5100 with the wound protector assembly 300. Latch assembly 5140 includes a coupler body 5142 with diametrically opposed vertically aligned spring loaded latches 5143, 5145. Each latch 5143, 5145 has a ratchet tooth 5152 at one end, a flexible arm 5156 on the opposing end and a middle portion 5154 therebetween to pivot around. The coupler body 5142 has an annular groove 5168 for flexible arm 5156 to mate with. This embodiment works similar to latch assembly 5040. To operate, a user squeezes flexible arm 5156 and pivots the latches 5143, 5145 outwardly such that ratchet teeth 5152 engage ratchet teeth 322 of retaining ring 312.

FIGS. 54-56 show an alternate embodiment of a latch assembly 5440 for mating the multi-port assembly 200 with the wound protector assembly 300. A spring loaded horizontal latch ring 5450 is configured to engage wound protector 300. More specifically, the latch ring 5450 includes a ratchet feature 5452 that can engage ratchet teeth 322 of wound protector 300. In an alternate embodiment, the ratchet feature may also simply mate with the elastic wound protector directly.

A button 5445 on the latch ring 5450 contains spring 5462 which manipulates the ratchet feature 5452. By pressing the button 5445, the ratchet feature 5452 is moved outwards (shown in FIG. 56) to an open position, and a user can either engage or disengage from the wound protector 300. Releasing the spring (shown in FIG. 55) returns the ratchet feature to a closed position and maintains the connection between ratchet feature 5452 and ratchet teeth 322. This embodiment also allows the user to reposition the top multi-port assembly 200 rotationally without losing the seal.

FIGS. 57-59 show yet another alternate embodiment for a latch assembly 5740. In this embodiment, a spring loaded hose clamp 5742 engages wound protector assembly 5900. In this embodiment, wound protector assembly 5900 includes an elastic body 5904 and a proximal ring 5904a that maintains the seal between multi-port assembly 5700 and the wound protector body 5904.

The hose clamp 5742 is embedded inboard of an inner ring 5736 (shown in FIG. 58), which in turn, is positioned inboard of an outer ring 5738. The outer ring 5738 mates the latch assembly 5740 to the multi-port sub assembly 5800. Each of the inner ring 5736 and outer ring 5738 include a finger tab 5736a, 5738a, respectively, to manipulate the clamp 5742. A user squeezes the tabs 5736a, 5738a towards one another (as shown in FIG. 59) which compresses the clamp 5742 to loosen the engagement from the wound protector body 5904. This design also allows the user to reposition the multi-port assembly 200 rotationally.

FIGS. 60-62 illustrate an alternate embodiment of multi-port sub assembly 6000 and wound protector sub assembly 6100 having a push on design with ratchet feature 6122. The elastic access portion 6010 is coupled to a top ring 6012 which has diametrically opposed release pads 6014 and inwardly protruding ratchet teeth 6022 along a bottom circumference thereof. The wound protector 6100 has a bottom ring 6132 at a proximal end 6104a of the wound protector body 6104 with ratchet features 6134.

To assemble and disassemble, a user squeezes the release pads 6014 inwards to flex the top ring 6012 and pushes the top ring 6012 over the bottom ring 6132 until ratchet teeth 6022 align with the ratchet features 6134. Releasing the pads 6014 will return the top ring 6012 to a home position and ratchet teeth 6022 of the top ring 6012 will lock with the ratchet features 6134 of the bottom ring 6132. To adjust rotation, the user squeezes the release pads 6014 and rotates the multi-port assembly 6000 until the desired position is reached.

With reference to FIGS. 63-66 another alternate embodiment of a multi-port assembly 6300 and wound protector sub assembly 6400 is shown. In this embodiment, retaining ring 6412 is part of the multi-port assembly, in contrast to the previous embodiments wherein the retaining ring was part of the wound protector assembly (for example as shown in FIGS. 1-15). With this design, a top ring 6432 is coupled to the elastic access portion 6410 and includes a ratchet button 6433. The ratchet button 6433 has two flexible hooks 6433a on opposing ends which engage a ratchet feature 6422 of the retaining ring 6412. The top ring 6432 further includes downwardly extending flexible tabs 6434 that snap over the ratchet feature 6422 and keep the top ring 6432 and elastic access portion 6410 from disengaging linearly. By pressing the ratchet button 6433 the hooks 6433a flex outwardly and allow rotational movement of the elastic access portion 6410.

The retaining ring 6412 includes press fit slots 6424 to accept a spring loaded shroud 6452 and a plurality of 90 degree cams slots 6426 for mating with wound protector 6400. The shroud 6452 has flexible arms 6454 which attach to the ratchet ring 6412 and bias the shroud 6452 away from the ratchet ring 6412. The wound protector 6400 has a bottom ring 6414 at a proximal end 6404a of the wound protector body 6404 without circumferentially arranged perpendicularly extending posts 6414a that mate with the cam slots 6426 of the ratchet ring 6412.

The shroud 6452 includes a plurality of cross-arms 6456 to engage the posts 6414a of the bottom ring 6414 as the posts 6414a are inserted into the cam slots 6426. As a user pushes and twists the multi-port sub assembly 6300 onto the wound protector 6400 the posts 6414a of wound protector 6400 migrate through the cam slots 6426 and the shroud 6456 extends over the proximal portion 6404a of the wound protector body 6404 thereby locking the multi-port sub assembly 6300 to the wound protector 6400. To remove, the user will lift the shroud 6456 away from the wound protector 6400, reverse twist and pull off.

FIGS. 67-69 show yet another alternate embodiment of a multi-port assembly 6700 and wound protector assembly 6800 having a push and twist design with three rotational positions. The multi-port assembly 6700 includes an inner ring 6714, and an outer ring 6716 attached thereto. The inner ring 6714 has a plurality of flexible arms 6722 (shown in FIG. 69) with a ratchet tooth 6724 on one end. Each ratchet tooth 6724 includes a perpendicularly extending post 6724a that engages a corresponding hole 6718 of outer ring 6716. The inner ring 6714 also has a plurality of 90 degree locking tabs 6732 (shown in FIG. 68) to lock the multi-port assembly 6700 to the wound protector sub assembly 6800.

The wound protector sub-assembly 6800 has a proximal flange 6812 extending from a proximal portion 6804a of the wound protector body 6404 that includes a plurality of elongated slots 6814 to accept the inner ring locking tabs 6732, and openings 6818 to accept the ratchet tooth 6724 of the inner ring 6714 therein. The openings 6818 are positioned as a set of three between the elongated slots 6814.

To assemble, a user positions the locking tabs 6732 of the inner ring 6714 over the elongated slots 6814 of the proximal flange 6812 and pushes downwardly and twists. The 90 degree shape of the locking tab 6732 will fit into a keyed portion 6814a of elongated slot 6814. The twisting motion locks the multi-port sub assembly 6700 to the wound protector 6800 (shown in FIG. 69). The elongated slot 6814 allows the user to continue to twist the multi-port sub assembly 6700 to three rotational positions corresponding to the openings 6818 along the proximal flange 6812. To remove, the user will lift the outer ring 6716 which will release the ratchet teeth 6724 out of the openings 6818 and reverse twist to migrate the locking tabs 6732 back to the keyed portion 6814a of the elongated slots 6814. The multi-port assembly 6700 can then be pulled away and off of the wound protector sub assembly 6800.

Figure 70:
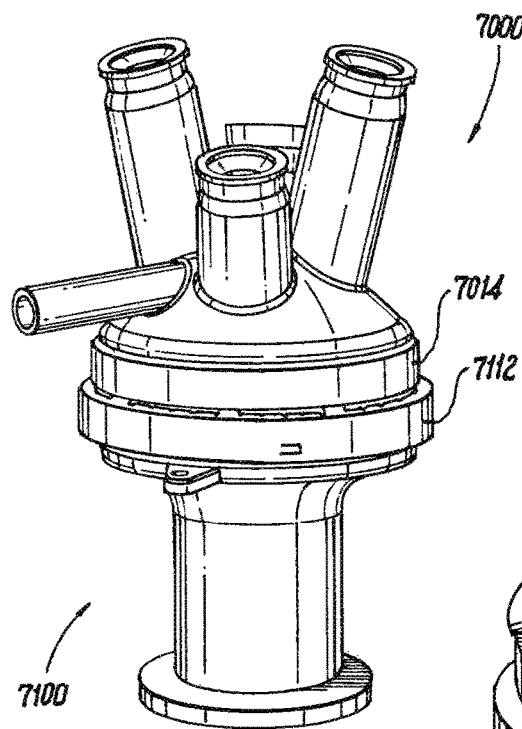
FIG. 70 is perspective view of an alternate embodiment of a latch assembly for a multi-port access device, showing a dynamic screw ring.
Figure 71:
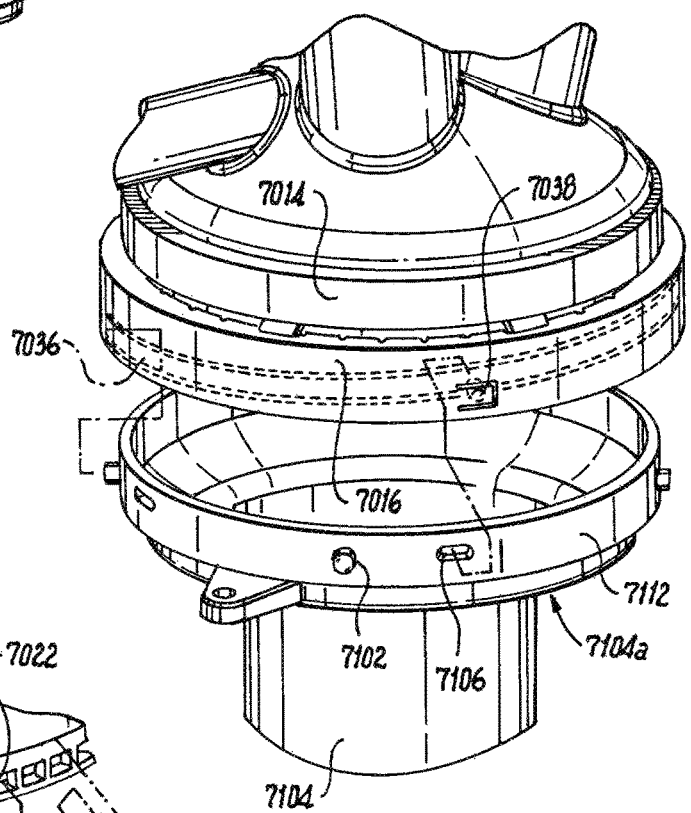
FIG. 71 is an exploded perspective view of the multi-port access device of FIG. 71, showing locking features on screw ring.
Figure 72:
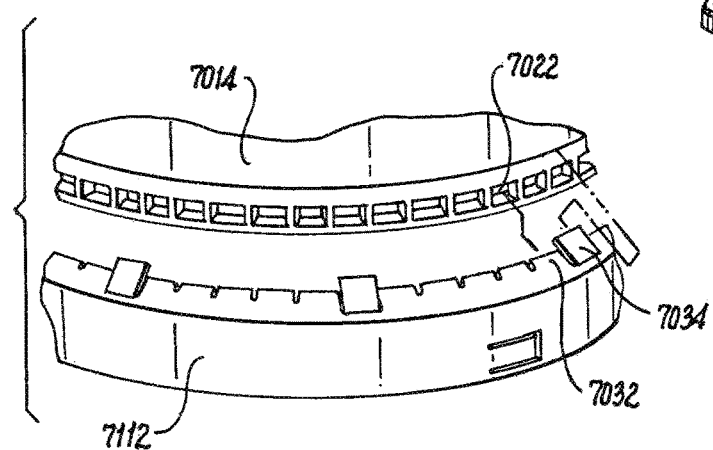
FIG. 72 is an exploded perspective view of the multi-port access device of FIG. 70, showing flexible tabs of the screw ring.

FIGS. 70-72 illustrate another alternate embodiment of a multi-port assembly 7000 and a wound protector sub assembly 7100. The multi-port assembly includes a static ring 7014 engaged with a dynamic ring 7016. The static ring 7014 has mating pockets 7022 to accept ratchet teeth 7032 of the dynamic ring 7016 therein (shown in FIG. 72). The dynamic ring 7016 also has flexible tabs 7034 to bias the ratchet teeth 7032 into the static ring 7014. In addition, the dynamic ring 7016 includes an internal thread 7036 and flexible locking features 7038 (shown in FIG. 71) to couple the multi-port assembly 7000 to the wound protector assembly 7100 and prevent linear movement therebetween.

The wound protector sub assembly 7100 includes posts 7102 and slots 7106 circumferentially spaced around a proximal ring 7112 at a proximal end 7104a of wound protector body 7104. A user screws the multi-port assembly 7000 over the posts 7102 on the proximal ring 7112 until the flexible locking tabs 7038 snap into mating slots 7106 on the proximal ring 7112. The top multi-port assembly 7000 is now locked onto the wound protector 7100.

To rotate the multi-port assembly 7000, the user pushes the static ring 7014 onto the dynamic ring 7016, which will flex the tabs 7034 of the dynamic ring and move the static ring slot/pockets 7022 off the dynamic ring ratchet teeth 7032 and allow rotation. To remove, the user flexes the locking feature 7038 on the dynamic ring 7016 to disengage the slot 7106 of the wound protector 7100 and twists the multi-port sub assembly to unscrew.

Figure 73:
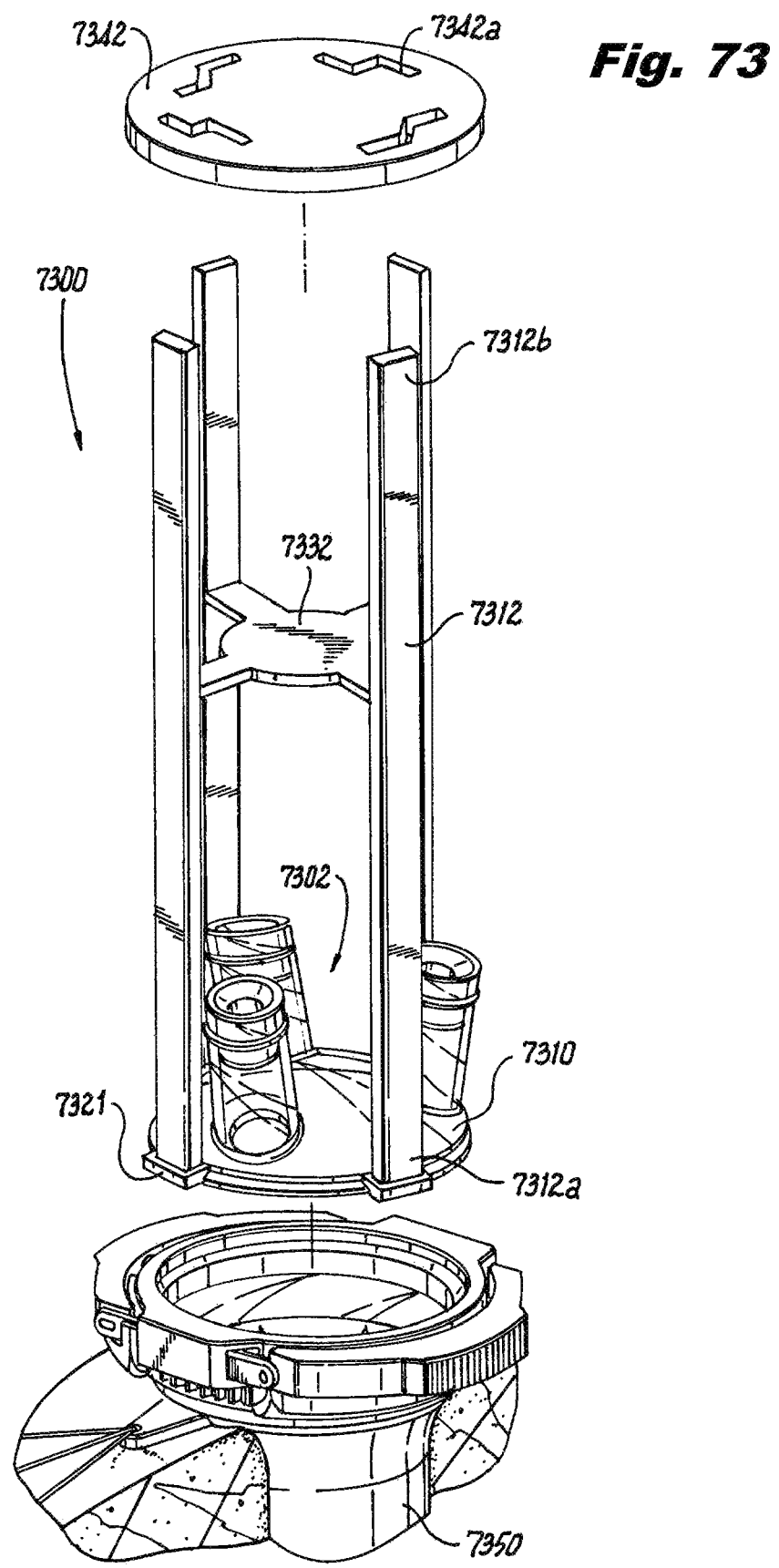
FIG. 73 is an exploded perspective view of an alternate embodiment for assembling a multi-port sub assembly, showing an assembly aid.

FIG. 73 illustrates an alternate design for assembling a multi-port assembly 7302 to the wound protector 7350. This embodiment includes an assembly aid 7300 that engages the elastic access portion 7310 of the multi-port assembly 7302. The assembly aid 7300 has four flexible arms 7312 which are attached together with a coupler 7332 that acts as a pivot for each of the flexible arms 7312. Each of the flexible arms 7312 has a first end 7312a that engages a corresponding slot 7321 of the elastic access portion 7310. By squeezing a second end 7312b of the each arm 7312, the arms 7312 pivot outward allowing the elastic access portion 7310 to assemble over the wound protector 7350. In an alternate embodiment, a rotational disc 7342 with openings for the flexible arms 7312 can be used to squeeze and pivot the flex arms 7312.

FIGS. 74-75 illustrate an alternate embodiment for a wound protector sub assembly 7400 having an adjustable length. More specifically, the wound protector assembly 7400 includes a plurality of telescoping sections 7404a-c biased closed with springs 7406b-c. The springs 7408b-c are held in position by a flange 7406b-c of each telescoping section. The flange of the outermost telescoping section 7406a anchors into the patient and extends through the incision to allow the multi-port sub assembly 200 to attach with retaining ring 312. Rotation of each telescoping section 7404a-c allows for adjusting the length of the wound protector assembly 7400.

Figure 76:
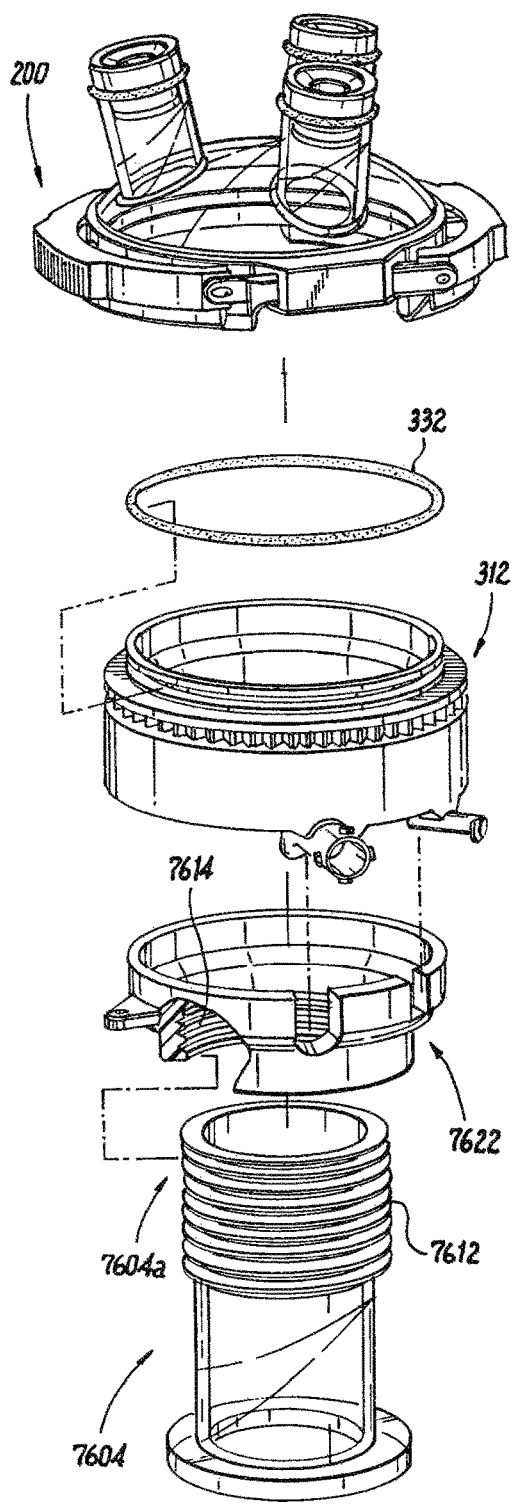
FIG. 76 is an exploded perspective view of an alternate embodiment of a multi-port access device, showing a threaded wound protector.

FIG. 76 illustrates an alternate embodiment for extending the length of a wound protector assembly 7600. In this embodiment an external thread 7612 positioned on a proximal portion 7604a of wound protector body 7604 is configured to engage an internal thread 7614 of a proximal ring 7622. The proximal ring 7622 can be lifted or lowered simply by twisting thereby adjusting the height of the multi-port sub assembly 200 as needed.

Figure 77:
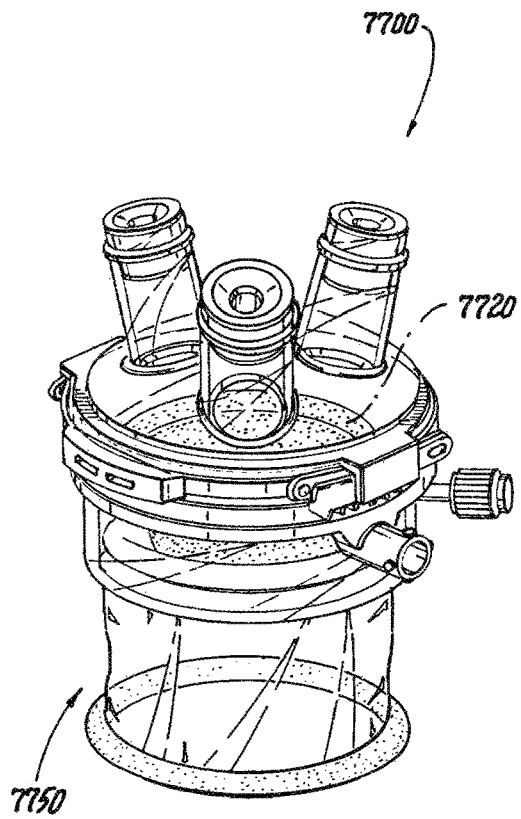
FIG. 77 is a perspective view of the multi-port access device of FIG. 76, showing the assembled device.

FIG. 77 shows another embodiment of a multi-port sub assembly and wound protector sub assembly which is particularly adapted for specimen removal. In this regard, the device includes an "S" shaped duckbill seal 7720. A similar type of seal structure is disclosed for example in U.S. Patent Application Publication No. 2013/0012782, the disclosure of which is herein incorporated by reference in its entirety.

Figure 78:
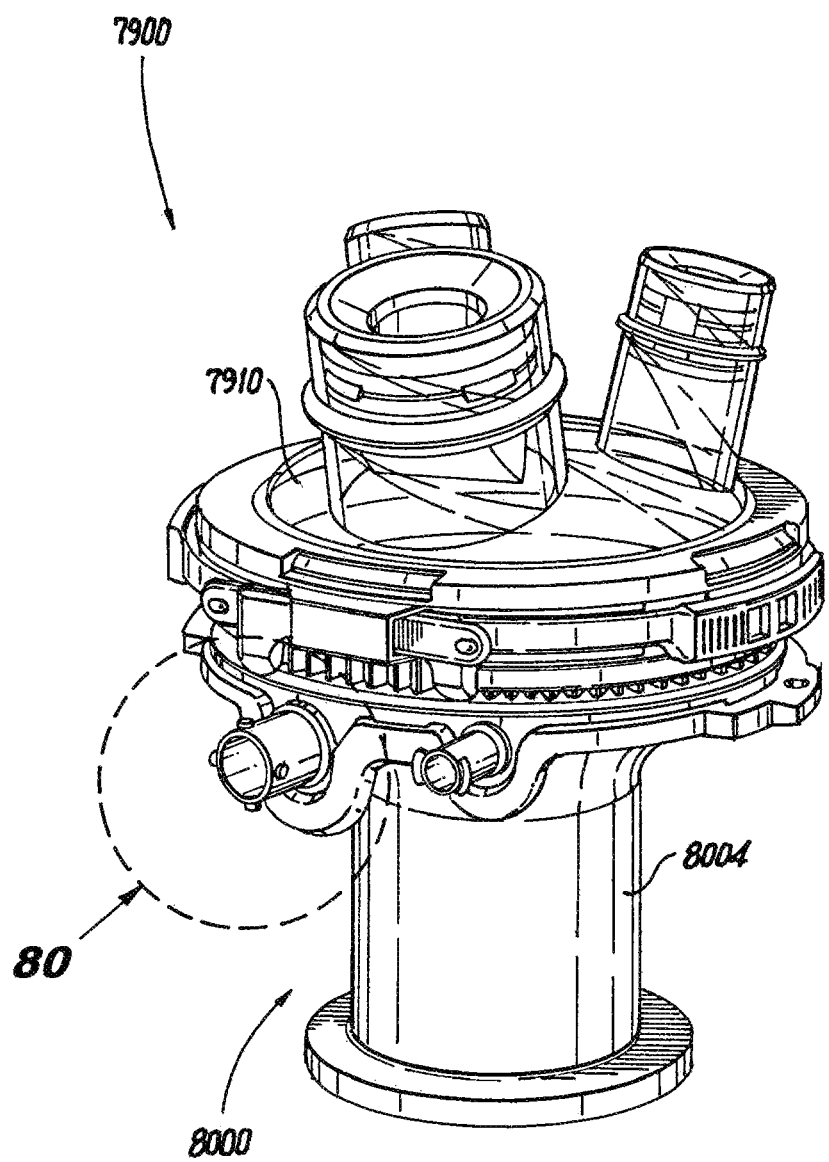
FIG. 78 is a perspective view of an alternate embodiment of a multi-port access device, having snap fit features for assembly.
Figure 79:
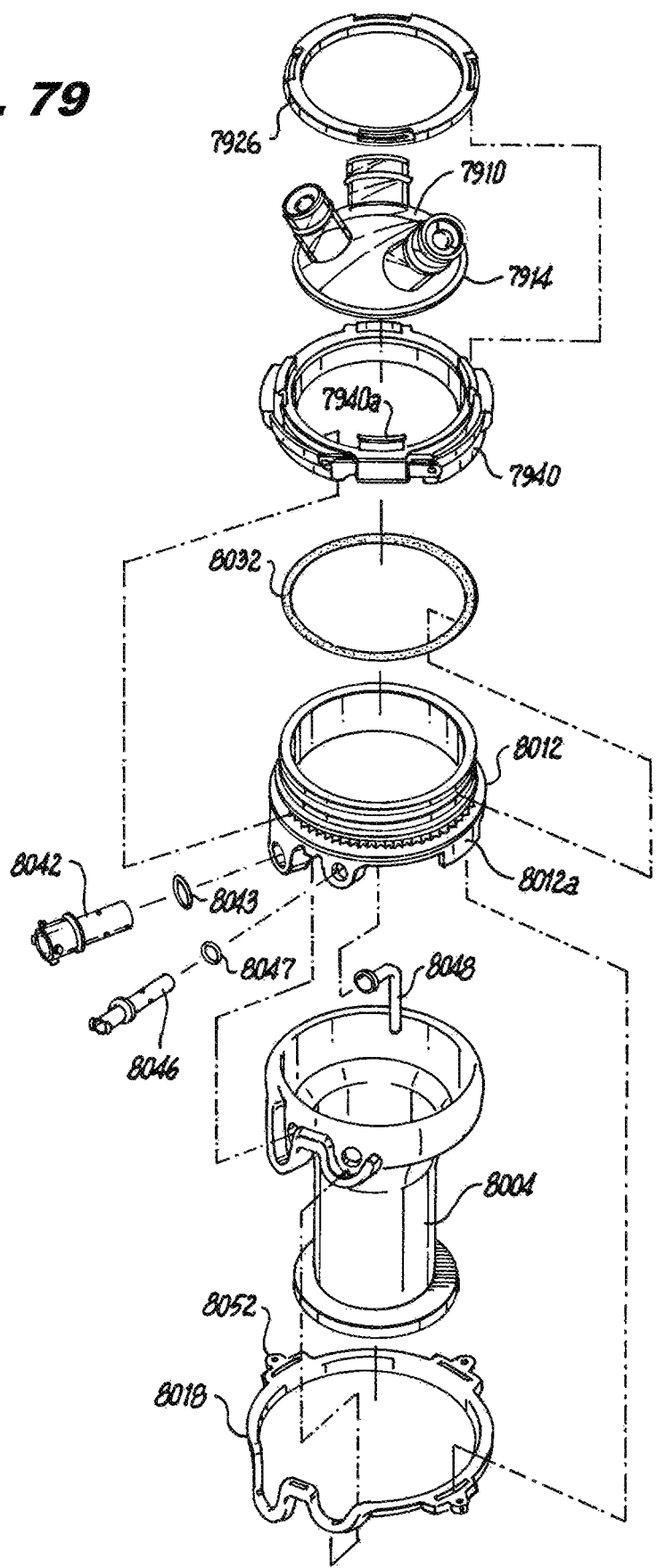
FIG. 79 is an exploded perspective view of the multi-port access device of FIG. 78, showing alignment between a top ring of a multi-port sub assembly and bottom ring of a wound protector assembly.
Figure 80:
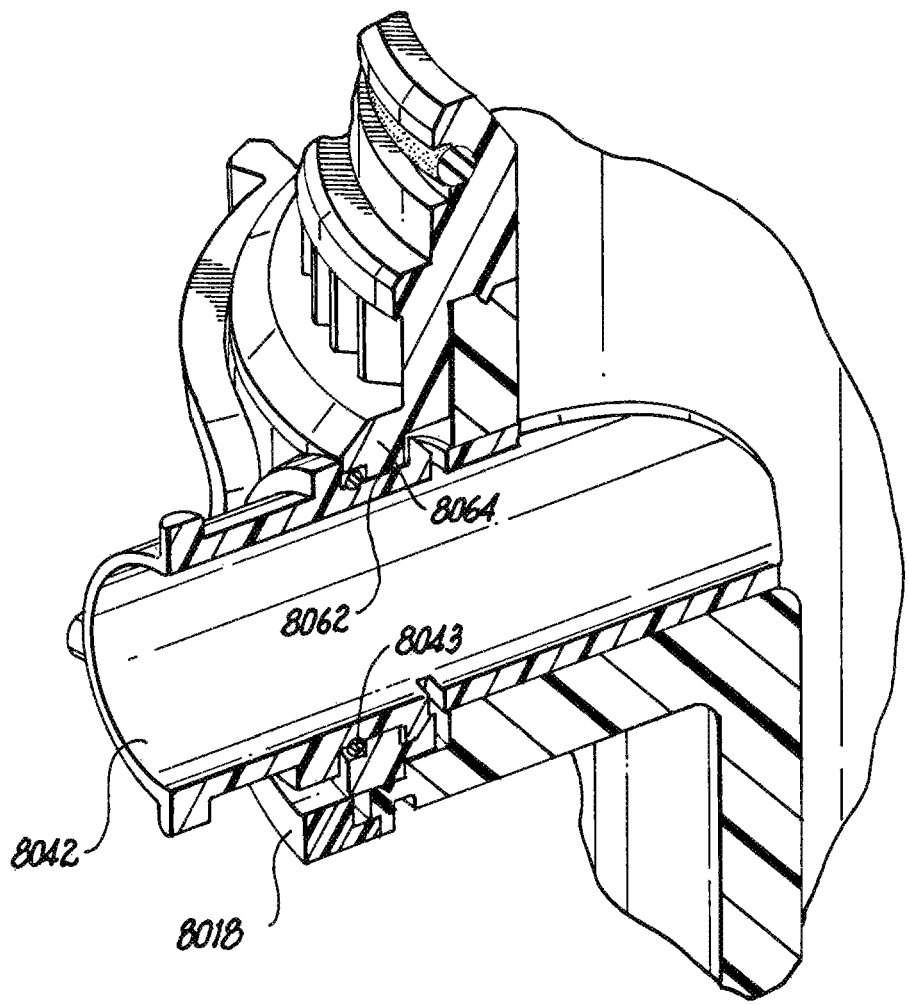
FIG. 80 is a detailed view of alignment of the multi-port sub assembly and wound protector assembly with air seal port.

Referring to FIGS. 78-80 another alternate embodiment of multi-port assembly 7900 and wound protector assembly 8000 is shown having snap fit features. As best seen in FIG. 80, multi-port sub assembly 7900 includes a top ring 7926 with a plurality of circumferentially spaced apart openings therethrough. Latch assembly 7940, similar to latch assembly 240, includes a plurality of circumferentially space upwardly extending flexible tabs 7940a designed and configured to snap fit into corresponding openings of the top ring. A flange 7914 on the elastic access portion 7910 of the multi-port end cap 7910 is squeezed between top ring 7926 and latch assembly 7940 securing the multi-port end cap therebetween.

Figure 81:
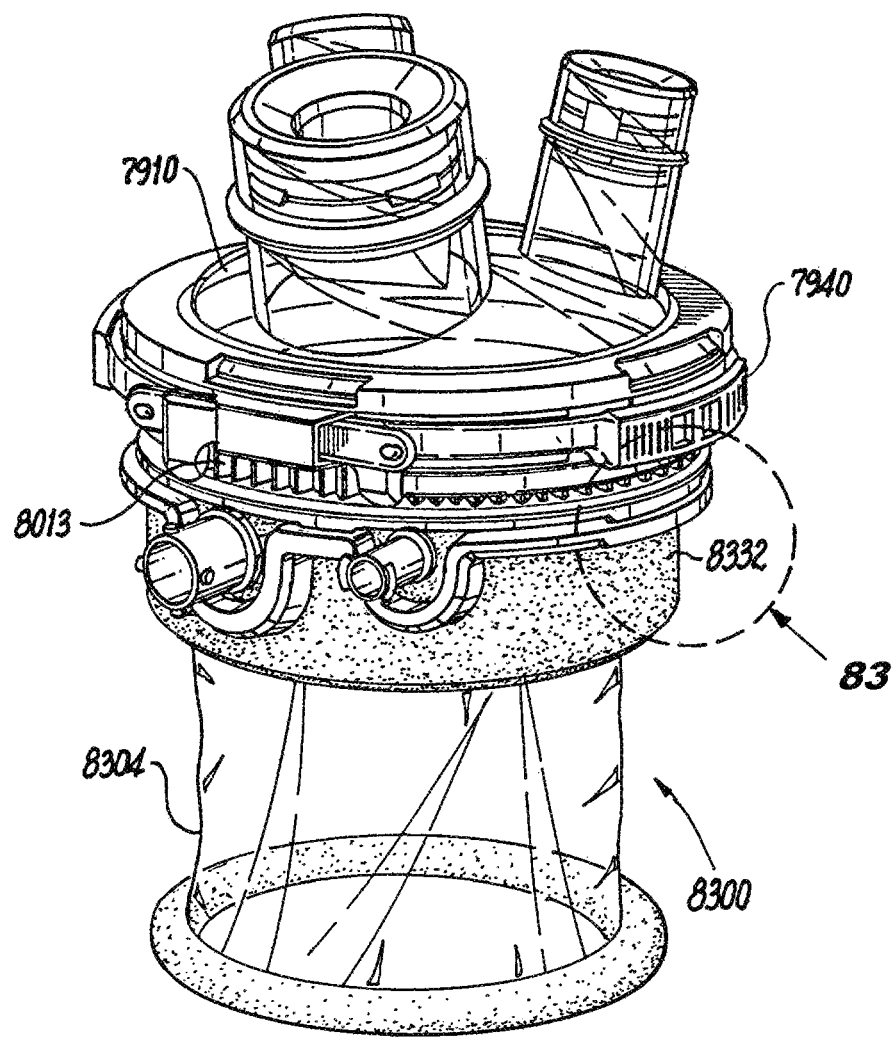
FIG. 81 is a perspective view of an alternate embodiment of a multi-port access device, having a seal therein.

Retaining ring 8012, similar to retaining ring 312, includes ratchet features 322 that engage with ratchet teeth 252 of the latch assembly 7940. A smoke evacuation port 8048 can be inserted into retaining ring 8012 with pressure sensing port 8046. As shown in FIG. 81, the air seal port 8042 includes an annular groove 8062 for mating with flex tabs 8064 of the retaining ring 8012. O-ring seals 8043, 8047 are positioned between the air seal port 8042 and pressure sensing port 8046, respectively, and the retaining ring 8012 to maintain the seal during a surgical procedure (shown best in FIG. 81).

Wound protector assembly 8000 includes a bottom ring 8018 having circumferentially spaced openings therethrough that allow flexible tabs 8012a of retaining ring 8012 to be snap fitted therein. An adapter 8034 is secured and held into position between the retaining ring 8012 and bottom ring 8018. Both the adapter 8034 and bottom ring 8318 are dimensioned and configured to allow air seal port 8042 and pressure sensing port 8046 to easily engage with the retaining ring 8012. As shown in FIG. 79, the adapter 8034 is a proximal portion of the wound protector body 8004, similar to wound protector 304, configured for insertion into a patient.

Figure 82:
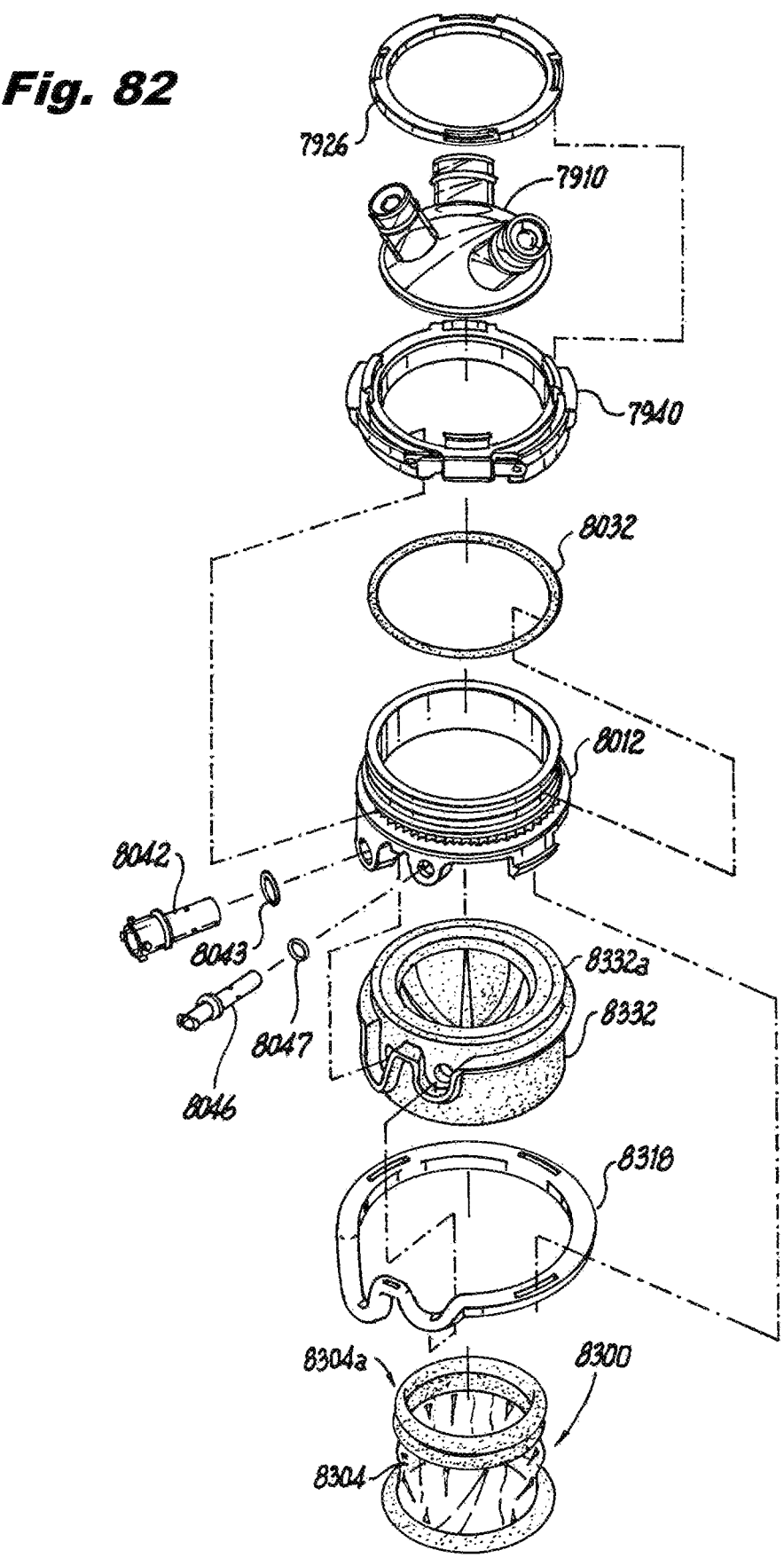
FIG. 82 is an exploded perspective view of the multi-port access device of FIG. 81, showing alignment between a top ring of a multi-port sub assembly and bottom ring of a wound protector assembly.

FIGS. 81-83 illustrate an alternate embodiment of wound protector assembly 8300. Wound protector assembly 8300 is coupled to multi-port sub assembly 7900. In this embodiment, adapter is in the form of a seal 8332 positioned between retaining ring 8012 and bottom ring 8318. Both the seal 8332 and bottom ring 8318 are dimensioned and configured to allow air seal port 8042 and pressure sensing port 8046 to easily engage with the retaining ring 8012.

Seal 8332 mates with a proximal portion 8304a of wound protector body 8304, similar to wound protector 1004. Bottom ring slides around seal 8332 and aligns with an annular flange or groove to further maintain seal in position. Referring to FIGS. 84 and 85 two seal configurations are shown capable of use with wound protector assembly 8300. Seal 8332 illustrates a duck bill design and seal 8334 illustrates a generally S shape.

While the subject invention have been shown and described with reference to a preferred embodiment, those skilled in the art will readily appreciate that various changes and/or modifications may be made thereto without departing from the spirit and scope of the subject invention as defined by the appended claims.

What is claimed is:

1. An access device for surgical procedures comprising:
   a) a tubular adapter having opposed proximal and distal end portions, wherein the tubular adapter has an annular flange adjacent the proximal end portion thereof that is secured between an upper retaining ring and a lower engagement ring;
   b) a multiport end cap including a plurality of separate access ports for accommodating the introduction of individual surgical instruments into an abdominal cavity of a patient;
   c) a latch assembly for operatively connecting the multiport end cap to the upper retaining ring, wherein the multiport end cap is secured between the latch assembly and a top securement ring; and
   d) a laparoscopic wound protector having a proximal portion that mates with the distal end portion of the tubular adapter and is configured for introduction through a single incision formed in a wall of the abdominal cavity of the patient.

2. An access device for surgical procedures as recited in claim 1, wherein a duckbill seal is operatively associated with the tubular adaptor.

3. An access device for surgical procedures as recited in claim 1, wherein the latch assembly is adapted and configured to permit relative axial rotation of the multiport end cap and the upper retaining ring associated with the tubular adapter.

4. An access device for surgical procedures as recited in claim 3, wherein the latch assembly includes a ratchet mechanism for selectively positioning the multiport end cap relative to the upper retaining ring associated with the tubular adapter.

5. An access device for surgical procedures as recited in claim 4, wherein the latch assembly includes spring loaded latches for selectively moving the ratchet mechanism.

6. An access device for surgical procedures as recited in claim 1, wherein the upper retaining ring supports a first connector port for a pressurized gas line and a second connector port for a pressure sensing line.

7. An access device for surgical procedures as recited in claim 1, wherein a seal assembly is operatively associated with each of the access ports of the end cap.

8. An access device for surgical procedures as recited in claim 1, wherein at least one of the access ports has a larger access diameter than the other access ports.

9. An access device for surgical procedures as recited in claim 1, wherein the top securement ring has a plurality of circumferentially spaced apart opening therein for mating with corresponding flexible tabs of the latch assembly to secure the multiport end cap therebetween.

10. An access device for surgical procedures as recited in claim 1, wherein the lower engagement ring has a plurality of circumferentially spaced apart opening therein for mating with corresponding flexible tabs of the upper retaining ring to secure the annular flange of the tubular adapter therebetween.

* * * * *